United States Patent
Tian et al.

(10) Patent No.: US 11,922,654 B2
(45) Date of Patent: Mar. 5, 2024

(54) MAMMOGRAPHIC IMAGE PROCESSING METHOD AND APPARATUS, SYSTEM AND MEDIUM

(71) Applicant: Tencent Technology (Shenzhen) Company Limited, Shenzhen (CN)

(72) Inventors: Kuan Tian, Shenzhen (CN); Cheng Jiang, Shenzhen (CN); Kezhou Yan, Shenzhen (CN); Rongbo Shen, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 390 days.

(21) Appl. No.: 17/367,266

(22) Filed: Jul. 2, 2021

(65) Prior Publication Data

US 2021/0338179 A1    Nov. 4, 2021

Related U.S. Application Data

(63) Continuation of application No. PCT/CN2020/088759, filed on May 6, 2020.

(30) Foreign Application Priority Data

May 16, 2019   (CN) .................. 201910407807.X

(51) Int. Cl.
*G06T 7/70* (2017.01)
*A61B 6/12* (2006.01)
(Continued)

(52) U.S. Cl.
CPC .................. *G06T 7/73* (2017.01); *A61B 6/12* (2013.01); *A61B 6/502* (2013.01); *G06F 18/24* (2023.01);
(Continued)

(58) Field of Classification Search
CPC ........... G06T 7/73; G06T 7/0012; G06T 7/70; G06T 2207/20084; G06T 2207/30068; G06T 2207/30096; G06V 2201/03
See application file for complete search history.

(56) References Cited

U.S. PATENT DOCUMENTS

| 8,759,783 B1 | 6/2014 | Sachs et al. |
| 11,761,877 B2 * | 9/2023 | Kim .................. C12Q 1/04 |
| | | 435/106 |

(Continued)

FOREIGN PATENT DOCUMENTS

| CN | 105979875 A | 9/2016 |
| CN | 106203488 A | 12/2016 |

(Continued)

OTHER PUBLICATIONS

Tencent Technology, WO, PCT/CN2020/088759, Aug. 5, 2020, 4 pgs.

(Continued)

*Primary Examiner* — Ming Y Hon
(74) *Attorney, Agent, or Firm* — Morgan, Lewis & Bockius LLP

(57) ABSTRACT

A computer device, obtains a mammographic image of a unilateral breast. The mammographic image includes a cranial-caudal (CC)-position mammographic image and a mediolateral-oblique (MLO)-position mammographic image. The computer device invokes a breast detection model to perform a prediction of a condition of the unilateral breast according to the CC-position mammographic image and the MLO-position mammographic image. The device obtains a prediction result of the unilateral breast, and generates and outputs a detection report that includes the prediction result.

20 Claims, 16 Drawing Sheets

(51) Int. Cl.

| | | |
|---|---|---|
| *G06F 18/24* | (2023.01) | |
| *G06N 3/08* | (2023.01) | |
| *G06T 7/00* | (2017.01) | |
| *G06T 7/73* | (2017.01) | |
| *G16H 15/00* | (2018.01) | |
| *G16H 30/20* | (2018.01) | |
| *G16H 30/40* | (2018.01) | |
| *G16H 50/20* | (2018.01) | |

(52) U.S. Cl.
CPC ............ *G06N 3/08* (2013.01); *G06T 7/0012* (2013.01); *G06T 7/70* (2017.01); *G16H 15/00* (2018.01); *G16H 30/20* (2018.01); *G16H 30/40* (2018.01); *G16H 50/20* (2018.01); *G06T 2207/10116* (2013.01); *G06T 2207/20084* (2013.01); *G06T 2207/30068* (2013.01); *G06T 2207/30096* (2013.01); *G06V 2201/03* (2022.01)

(56) References Cited

U.S. PATENT DOCUMENTS

| | | | | |
|---|---|---|---|---|
| 2006/0034503 | A1* | 2/2006 | Shimayama | .......... G06T 7/0012 |
| | | | | 382/132 |
| 2007/0003119 | A1 | 1/2007 | Roehrig et al. | |
| 2009/0086891 | A1* | 4/2009 | Ofuji | ...................... G06T 7/0012 |
| | | | | 378/37 |
| 2012/0166211 | A1* | 6/2012 | Park | ...................... G16H 50/20 |
| | | | | 705/2 |
| 2016/0104280 | A1* | 4/2016 | Buelow | ...................... G06T 7/33 |
| | | | | 382/131 |
| 2018/0070892 | A1* | 3/2018 | Sugiyama | .............. A61B 6/502 |
| 2018/0166161 | A1* | 6/2018 | Sami | ................ G06Q 10/06311 |
| 2019/0388047 | A1* | 12/2019 | Morita | .................. A61B 6/5205 |
| 2020/0037885 | A1* | 2/2020 | Subbhuraam | ........ A61B 5/7264 |
| 2020/0160970 | A1* | 5/2020 | Lyman | ...................... G06T 3/40 |
| 2020/0219237 | A1* | 7/2020 | Ramsay | .................. G16H 30/40 |
| 2020/0315587 | A1* | 10/2020 | Toporek | .................. A61B 8/5269 |
| 2021/0248744 | A1* | 8/2021 | Rijken | .................. A61B 5/7267 |
| 2023/0287370 | A1* | 9/2023 | Zhang | .................... C12N 15/11 |
| | | | | 435/462 |

FOREIGN PATENT DOCUMENTS

| | | |
|---|---|---|
| CN | 106339591 A | 1/2017 |
| CN | 108392215 A | 8/2018 |
| CN | 108765387 A | 11/2018 |
| CN | 109598702 A | 4/2019 |
| CN | 109993170 A | 7/2019 |
| CN | 110136829 A | 8/2019 |

OTHER PUBLICATIONS

Tencent Technology, IPRP, PCT/CN2020/088759, Nov. 16, 2021, 5 pgs.

"Tencent's Exploration in the Direction of Breast Cancer Imaging AI Diagnosis", Tencent Technical Engineering Official Account, Apr. 22, 2018, Retrieved from the Internet: https://cloud.tencent.com/developer/article/1105790.

Tencent Technology, ISR, PCT/CN2020/088759, Aug. 5, 2020, 3 pgs.

* cited by examiner

MAMMOGRAPHIC IMAGE PROCESSING METHOD AND APPARATUS, SYSTEM AND MEDIUM

CROSS-REFERENCE TO RELATED APPLICATIONS

This application is a continuation application of PCT Application No. PCT/CN2020/088759, filed on May 6, 2020, entitled "MAMMOGRAPHIC IMAGE PROCESSING METHOD AND APPARATUS, SYSTEM AND MEDIUM," which claims priority to Chinese Patent Application No. 201910407807.X, entitled "MAMMOGRAPHIC IMAGE ASSISTED DIAGNOSIS METHOD AND APPARATUS, SYSTEM AND MEDIUM" and filed with the China National Intellectual Property Administration on May 16, 2019, all of which are incorporated by reference herein in their entirety.

FIELD OF THE TECHNOLOGY

Embodiments of this application relate to the field of artificial intelligence, and in particular, to a mammographic image processing method and apparatus, a system and a computer-readable storage medium.

BACKGROUND OF THE DISCLOSURE

Mammographic images are widely used in early breast cancer screening. Doctors would usually diagnose all kinds of abnormality information in the mammographic images, including lump lesions, calcified lesions, lymph node enlargement and skin abnormalities, etc., and give breast imaging reporting and data system (BI-RADS) gradings representing degrees of risks according to the abnormality information.

In related art, a neural network model is adopted to recognize abnormality areas in a mammographic image to position the abnormality areas in the mammographic image and obtain corresponding abnormality information, inferring an overall BI-RADS score of the mammographic image based on all the abnormality information in the mammographic image.

However, the prediction process of the foregoing neural network model is only a simple prediction process on a two-dimensional image level, which is not consistent with the actual film viewing process of doctors, resulting in a low degree of accuracy in recognition of the abnormality areas.

SUMMARY

Embodiments of this application provide a mammographic image assisted diagnosis method and apparatus, a computer device, a system and a medium, and a mammographic image processing method and apparatus, a computer device, a system and a medium.

In accordance with some embodiments, a mammographic image assisted diagnosis method is performed by a computer device. The method comprises:
  obtaining a mammographic image of a unilateral breast, the mammographic image including: a cranial-caudal (CC)-position mammographic image and a mediolateral-oblique (MLO)-position mammographic image;
  invoking a breast detection model to perform a prediction of a condition of the unilateral breast according to the CC-position mammographic image and the MLO-position mammographic image, to obtain a benign and malignant prediction result of the unilateral breast;
  obtaining a prediction result of the unilateral breast, including a benign or malignant condition of the breast; and
  generating and outputting a detection report that includes the prediction result of the unilateral breast.

In accordance with some embodiments, a mammographic image assisted diagnosis apparatus comprises:
  an image obtaining module, configured to obtain a mammographic image of a unilateral breast, the mammographic image including: a CC-position mammographic image and an MLO-position mammographic image;
  a breast benign and malignant detection model, configured to perform benign and malignant prediction on the CC-position mammographic image and the MLO-position mammographic image, to obtain a benign and malignant prediction result of the unilateral breast; and
  an automatic report output module, configured to generate and output a detection report, the detection report including the benign and malignant prediction result of the unilateral breast.

In accordance with some embodiments, a computer device comprises one or more processors and memory. The memory stores one or more programs (e.g., computer-readable instructions) that, when executed by the one or more processors, cause the one or more processors to perform any of the methods disclosed herein.

In accordance with some embodiments, a mammographic image assisted diagnosis system, comprises: a breast DR device, a computer device, and a doctor device; the breast DR device being connected to the computer device, and the computer device being connected to the doctor device; the computer device including a memory and a processor; the memory storing computer-readable instructions, and the computer-readable instructions being loaded and executed by the processor to implement the foregoing mammographic image assisted diagnosis method.

In accordance with some embodiments, a non-transitory computer-readable storage medium stores computer-readable instructions that, when executed by one or more processors of a computing device, cause the one or more processors to perform any of the methods disclosed herein.

In accordance with some embodiments, a mammographic image processing method is performed by a computer device, the method including:
  obtaining a mammographic image of a unilateral breast, the mammographic image including: a cranial-caudal (CC)-position mammographic image and a mediolateral-oblique (MLO)-position mammographic image;
  invoking a target detection model to process the CC-position mammographic image and the MLO-position mammographic image, to obtain an image detection result of the unilateral breast; and
  generating a detection report according to the image detection result and outputting the detection report.

In accordance with some embodiments, a mammographic image processing apparatus comprises:
  an image obtaining module, configured to obtain a mammographic image of a unilateral breast, the mammographic image including: a cranial-caudal (CC)-position mammographic image and a mediolateral-oblique (MLO)-position mammographic image;
  a target detection model, configured to process the CC-position mammographic image and the MLO-position mammographic image, to obtain an image detection result of the unilateral breast; and an automatic report output module, configured to generate a detection report according to the image detection result and output the detection report.

In accordance with some embodiments, a computer device includes memory and a processor, the memory storing computer-readable instructions, the processor, when executing the computer-readable instructions, implementing operations of the mammographic image processing method.

In accordance with some embodiments, a mammographic image processing system includes: a breast DR device, a computer device, and a doctor device; the breast DR device being connected to the computer device, and the computer device being connected to the doctor device; the computer device including a memory and a processor; the memory storing computer-readable instructions, the processor, when executing the computer-readable instructions, implementing steps of the mammographic image processing method.

In accordance with some embodiments, a non-transitory computer-readable storage medium, storing computer-readable instructions, the computer-readable instructions, when executed by a processor, implementing operations of the foregoing mammographic image processing method.

Details of one or more embodiments of this application are provided in the accompanying drawings and descriptions below. Other features, objectives, and advantages of this application become apparent from the specification, the accompanying drawings, and the claims.

BRIEF DESCRIPTION OF THE DRAWINGS

To describe the technical solutions in the embodiments of this application more clearly, the following briefly introduces the accompanying drawings required for describing the embodiments. Apparently, the accompanying drawings in the following description show only some embodiments of this application, and a person of ordinary skill in the art may still derive other accompanying drawings from these accompanying drawings without creative efforts.

DESCRIPTION OF EMBODIMENTS

To make objectives, technical solutions, and advantages of the embodiments of this application clearer, the following further describes in detail implementations of this application with reference to the accompanying drawings.

Although terms such as "first" and "second" are used to describe various elements in the following description, these elements are not to be limited to these terms. These terms are merely used for distinguishing one element from another element. For example, a first image may be referred to as a second image, and similarly, a second image may be referred to as a first image without departing from the scope of the various examples. Both the first image and the second image may be images, and in some cases, may be separate and different images.

Terms used in description of the various examples in this specification are merely for describing specific examples and are not intended to impose limitations. As used in the description of the various examples and the appended claims, singular forms, "a" or "an" and "the", are intended to also include plural forms, unless the context clearly indicates otherwise. It is to be further understood that as used herein, the term "and/or" refers to and includes any and all possible combinations of one or more of the associated listed items. It is to be further understood that the terms "includes", "including", "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Based on the context, the term "if" may be interpreted as a meaning of "when" or "upon", "in response to determining", or "in response to detecting". Similarly, based on the context, the phrase "if determining" or "if detecting (a stated condition or event)" may be interpreted as a meaning of "when determining . . . ", "in response to determining . . . ", "when detecting (a stated condition or event)", or "in response to detecting (a stated condition or event)".

First, several terms described in the embodiments of this application are briefly introduced.

Mammographic image: It is an image obtained by projecting a two-dimensional image of a breast on an X-ray film by using the physical properties of X-rays and the different equidensity values of human breast tissue, referred to as a mammographic image for short.

Depending on different view positions, the mammographic image includes: a CC-position mammographic image and an MLO-position mammographic image.

Figure 1:
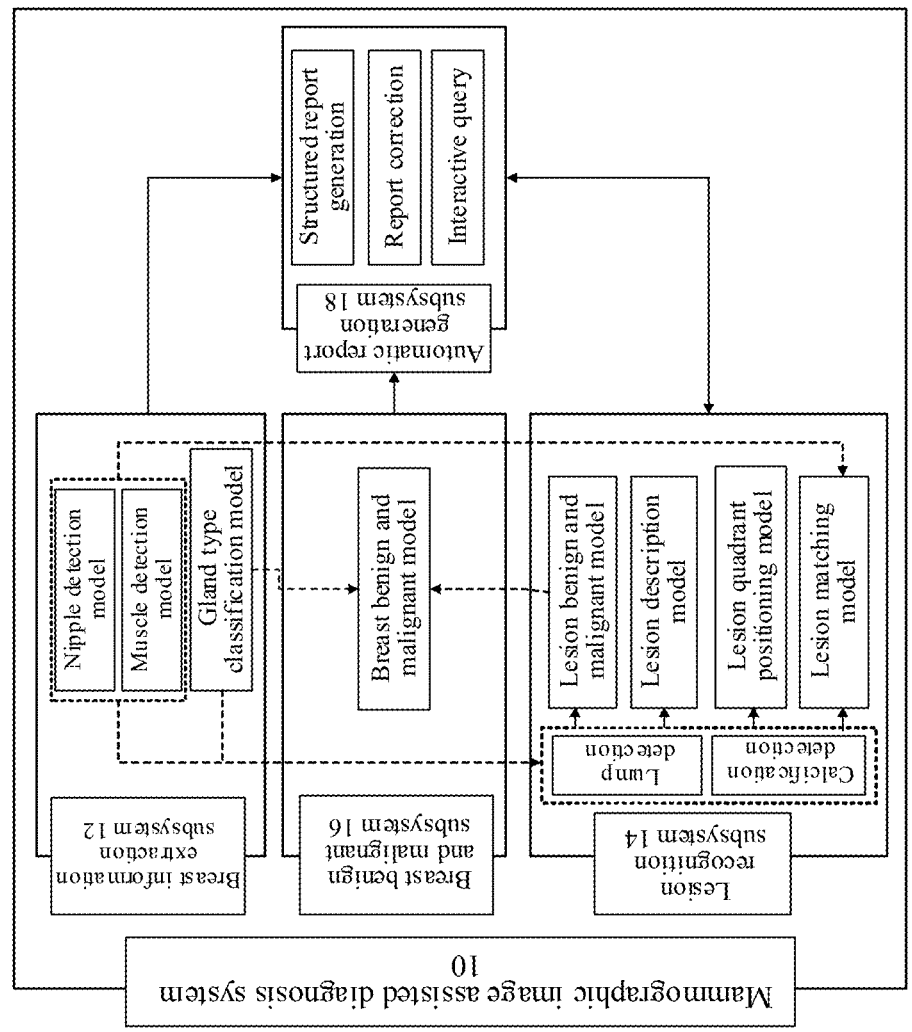
FIG. 1 is a flowchart of a mammographic image assisted diagnosis method according to an exemplary embodiment of this application.
Figure 1:
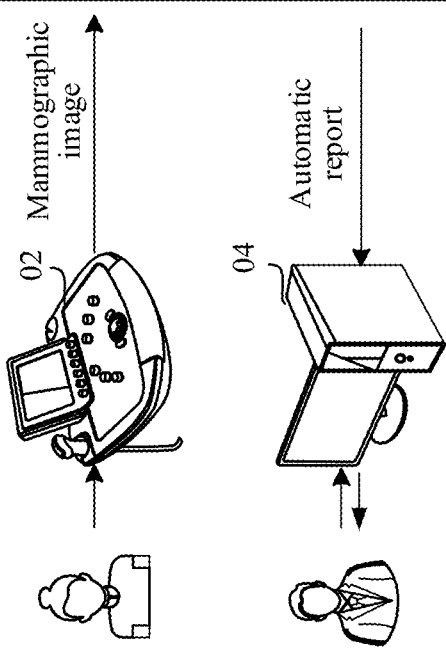

FIG. 1 is a structural block diagram of a computer system according to an exemplary embodiment of this application. The computer system includes: a breast digital radiography (DR) device 02, a mammographic image assisted diagnosis system 10, and a doctor device 04.

The breast DR device 02 is a device for collecting mammographic images based on a digital X-ray imaging technology. The breast DR device 02 may belong to the mammographic image assisted diagnosis system 10, and may also be deployed independently of the mammographic image assisted diagnosis system 10. In FIG. 1, independent deployment is taken as an example for illustration.

The mammographic image assisted diagnosis system 10 is one or more computer devices, such as at least one of a single server, a server group, and a server cluster. The system 10 includes at least one of a breast information extraction subsystem 12, a lesion recognition subsystem 14, a breast benign and malignant subsystem 16, and an automatic report regeneration subsystem 18.

The breast information extraction subsystem 12 is configured to extract overall breast information. The subsystem 12 includes: a nipple position detection model, a muscle position detection model, and a gland type classification model. The nipple position detection model and the muscle position detection model can be realized as the same neural network model, i.e., a nipple and muscle detection model.

The lesion recognition subsystem 14 is configured to perform lump detection and calcification detection on the mammographic image. A threshold is selected in consideration of a gland type of the breast in the detection process. The lesion recognition subsystem 14 performs lesion benign and malignant analysis, lesion attribute description, and CC-position lesion and MLO-position lesion matching on a detected lesion. In addition, the quadrant where the lesion is located is also positioned according to the nipple position and the muscle position.

The breast benign and malignant subsystem 16 is configured to perform benign and malignant prediction on a unilateral breast based on the lesion benign and malignant analysis subsystem 14 in combination with the CC-position mammographic image and the MLO-position mammographic image. The breast benign and malignant subsystem 16 includes a breast benign and malignant detection model. In some embodiments, the breast benign and malignant detection model dynamically selects a prediction threshold according to the gland type of the breast during prediction.

The automatic report generation subsystem 18 is configured to fuse all prediction results of the foregoing three subsystems to generate a structured detection report. A doctor can correct the generated detection report, and can select a mammographic image area of interest, and obtain relevant information of the mammographic image area through interactive query.

The doctor device 04 is a computer device used by a doctor, which may be a desktop computer, a notebook, a touch screen, and the like. The doctor device 04 is configured to view the detection report generated by the automatic report generation subsystem 18 and perform corresponding human-computer interaction. The doctor device 04 can be part of the mammographic image assisted diagnosis system 10, and may also be deployed independently of the mammographic image assisted diagnosis system 10. In FIG. 1, independent deployment is taken as an example for illustration.

Figure 2:
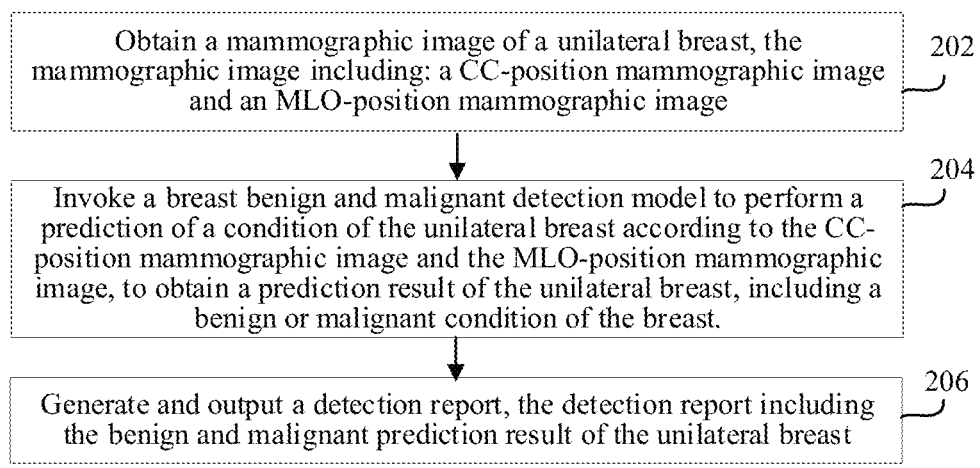
FIG. 2 is a flowchart of a mammographic image assisted diagnosis method according to another exemplary embodiment of this application.

FIG. 2 is a flowchart of a mammographic image assisted diagnosis method according to an exemplary embodiment of this application. The method may be applied to the mammographic image assisted diagnosis system shown in FIG. 1 (hereinafter referred to as a computer device for short). The method includes the following steps:

Step 202: obtain a mammographic image of a unilateral breast, the mammographic image including: a CC-position mammographic image and an MLO-position mammographic image.

The computer device obtains mammographic images of the unilateral breast on two different view positions. In some embodiments, the mammographic images on two different view positions include a CC-position mammographic image and an MLO-position mammographic image. The CC-position mammographic image is a mammographic image collected at a cranial-caudal position. The center line of the CC-position mammographic image is from top to bottom and enters the center of the film vertically from above the breast. The MLO-position mammographic image is a mammographic image collected at a mediolateral-oblique position. The center line of the MLO-position mammographic image enters the center of the film vertically through the inner side of the breast.

Step 204: invoke a breast benign and malignant detection model to perform a prediction of a condition of the unilateral breast according to the CC-position mammographic image and the MLO-position mammographic image. For example, the prediction includes a prediction of a benign or malignant condition of the breast.

In some embodiments, the breast benign and malignant detection model includes: a first single image detection component 22, a second single image detection component 24, a pooling layer 26, and a fully connected layer 28.

The computer device invokes the first single image detection component 22 to process the CC-position mammographic image to obtain a first feature (such as a first logits feature), and invokes the second single image detection component 24 to process the MLO-position mammographic image to obtain a second feature (such as a second logits feature). The computer device inputs the first feature and the second feature into the pooling layer 26 and the fully connected layer 28 to obtain the benign and malignant prediction result of the unilateral breast.

Step 206: generate and output a detection report, the detection report including the benign and malignant prediction result of the unilateral breast.

In conclusion, according to the method provided in this embodiment, the CC-position mammographic image and the MLO-position mammographic image of the unilateral breast are obtained; the breast benign and malignant detection model is invoked to perform a prediction of a condition of the unilateral breast according to on CC-position mammographic image and the MLO-position mammographic image, to obtain a prediction result of the unilateral breast, including a benign or malignant condition of the breast; and the detection report is generated, the detection report including the benign and malignant prediction result of the unilateral breast. Because the breast benign and malignant detection model can comprehensively perform benign and malignant prediction on the CC-position mammographic image and the MLO-position mammographic image, that is, mammographic images in two different views are combined for benign and malignant prediction, the actual film viewing process of the doctor is more realistically simulated, improving the accuracy of the benign and malignant prediction of the unilateral breast.

In some embodiments based on FIG. 2, the computer device invokes a gland type classification model to recognize a gland type in the mammographic image to obtain a gland type recognition result; and determine a prediction threshold corresponding to the breast benign and malignant detection model according to the gland type recognition result; and invoke the breast benign and malignant detection model after determining the prediction threshold to perform benign and malignant prediction on the CC-position mammographic image and the MLO-position mammographic image, to obtain the benign and malignant prediction result of the unilateral breast.

Figure 4:
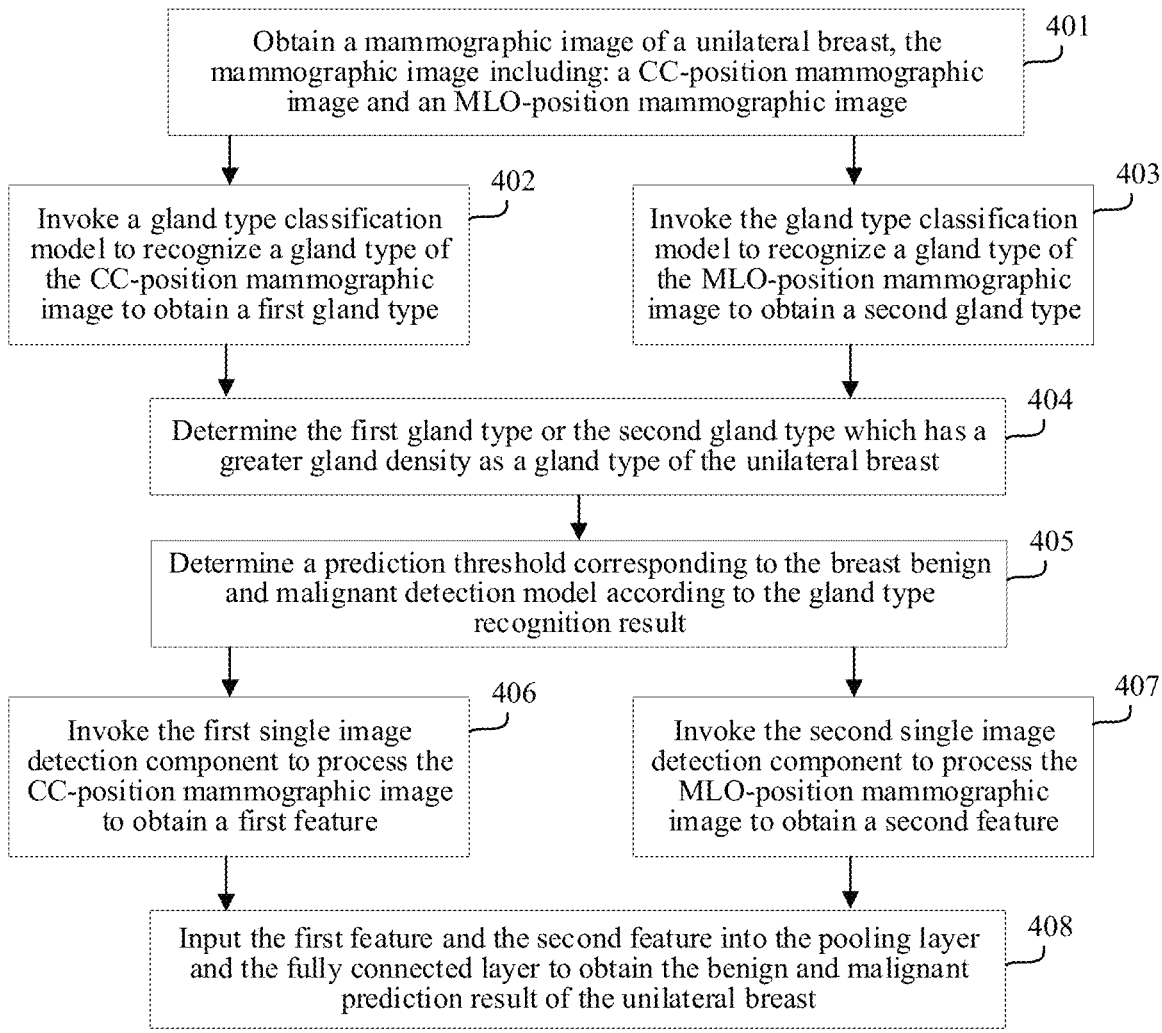
FIG. 4 is a flowchart of a mammographic image assisted diagnosis method according to another exemplary embodiment of this application.

FIG. 4 is a flowchart of a mammographic image assisted diagnosis method according to an exemplary embodiment of this application. The method may be applied to the mammographic image assisted diagnosis system shown in FIG. 1 (hereinafter referred to as a computer device). The method includes the following steps:

Step 401: obtain a mammographic image of a unilateral breast, the mammographic image including: a CC-position mammographic image and an MLO-position mammographic image.

The computer device obtains the mammographic image of the unilateral breast from a breast DR device. Alternatively, the computer device obtains the mammographic image of the unilateral breast from a doctor device.

The unilateral breast refers to the left breast or the right breast. When the unilateral breast is the left breast, the computer device obtains the mammographic image of the left breast. When the unilateral breast is the right breast, the computer device obtains the mammographic image of the right breast.

Step 402: invoke a gland type classification model to recognize a gland type of the CC-position mammographic image to obtain a first gland type.

The first gland type includes any one of a fat type, a small gland quantity type, a large gland quantity type, and a dense type.

Step 403: invoke the gland type classification model to recognize a gland type of the MLO-position mammographic image to obtain a second gland type.

The second gland type includes any one of a fat type, a small gland quantity type, a large gland quantity type, and a dense type.

Step 404: determine the first gland type or the second gland type which has a greater gland density as a gland type of the unilateral breast.

In some embodiments, the sequence of the gland densities of the four gland types in descending order is: dense type>small gland quantity type>large gland quantity type>fat type.

In some embodiments, if the first gland type is a glandular type, and the second gland type is the small gland quantity type, the glandular type is determined as the gland type of the unilateral breast. In some other embodiments, if the first gland type is the dense type, and the second gland type is the fat type, the dense type is determined as the gland type of the unilateral breast.

Step 405: determine a prediction threshold corresponding to the breast benign and malignant detection model according to the gland type recognition result.

There is a probability threshold for benign and malignant detection in the breast benign and malignant detection model, and the computer device determines the corresponding prediction threshold according to the gland type recognition result. In some embodiments, the fat type corresponds to a first threshold, the small gland quantity type corresponds to a second threshold, the large gland quantity type corresponds to a third threshold, and the dense type corresponds to a fourth type.

When the gland type of the unilateral breast is the fat type, the computer device determines the prediction threshold corresponding to the breast benign and malignant detection model as the first threshold. When the gland type of the unilateral breast is the small gland quantity type, the computer device determines the prediction threshold corresponding to the breast benign and malignant detection model as the second threshold. When the gland type of the unilateral breast is the large gland quantity type, the computer device determines the prediction threshold corresponding to the breast benign and malignant detection model as the third threshold. When the gland type of the unilateral breast is the dense type, the computer device determines the prediction threshold corresponding to the breast benign and malignant detection model as the fourth threshold.

Step 406: invoke the first single image detection component to process the CC-position mammographic image to obtain a first feature.

Step 407: invoke the second single image detection component to process the MLO-position mammographic image to obtain a second feature.

Step 408: input the first feature and the second feature into the pooling layer and the fully connected layer to obtain the benign and malignant prediction result of the unilateral breast.

Exemplarily, taking the prediction threshold of 60% as an example, when the benign and malignant prediction probability outputted by the fully connected layer is 65%, since 65% is greater than 60%, it is determined that the benign and malignant prediction result is malignant. When the benign and malignant prediction probability outputted by the fully connected layer is 40%, since 40% is less than 60%, it is determined that the benign and malignant prediction result is benign.

The prediction threshold can be dynamically changed according to the gland type.

In conclusion, according to the method, the CC-position mammographic image and the MLO-position mammographic image of the unilateral breast are obtained; the breast benign and malignant detection model is invoked to perform benign and malignant prediction on the CC-position mammographic image and the MLO-position mammographic image, to obtain the benign and malignant prediction result of the unilateral breast; and the detection report is generated, the detection report including the benign and malignant prediction result of the unilateral breast. Because the breast benign and malignant detection model can comprehensively perform benign and malignant prediction on the CC-position mammographic image and the MLO-position mammographic image, that is, mammographic images in two different views are combined for benign and malignant prediction, the actual film viewing process of the doctor is more realistically simulated, improving the accuracy of the benign and malignant prediction of the unilateral breast.

The foregoing neural network models and corresponding methods for training the neural network models are introduced below.

For a Breast Information Extraction Subsystem

Figure 5:
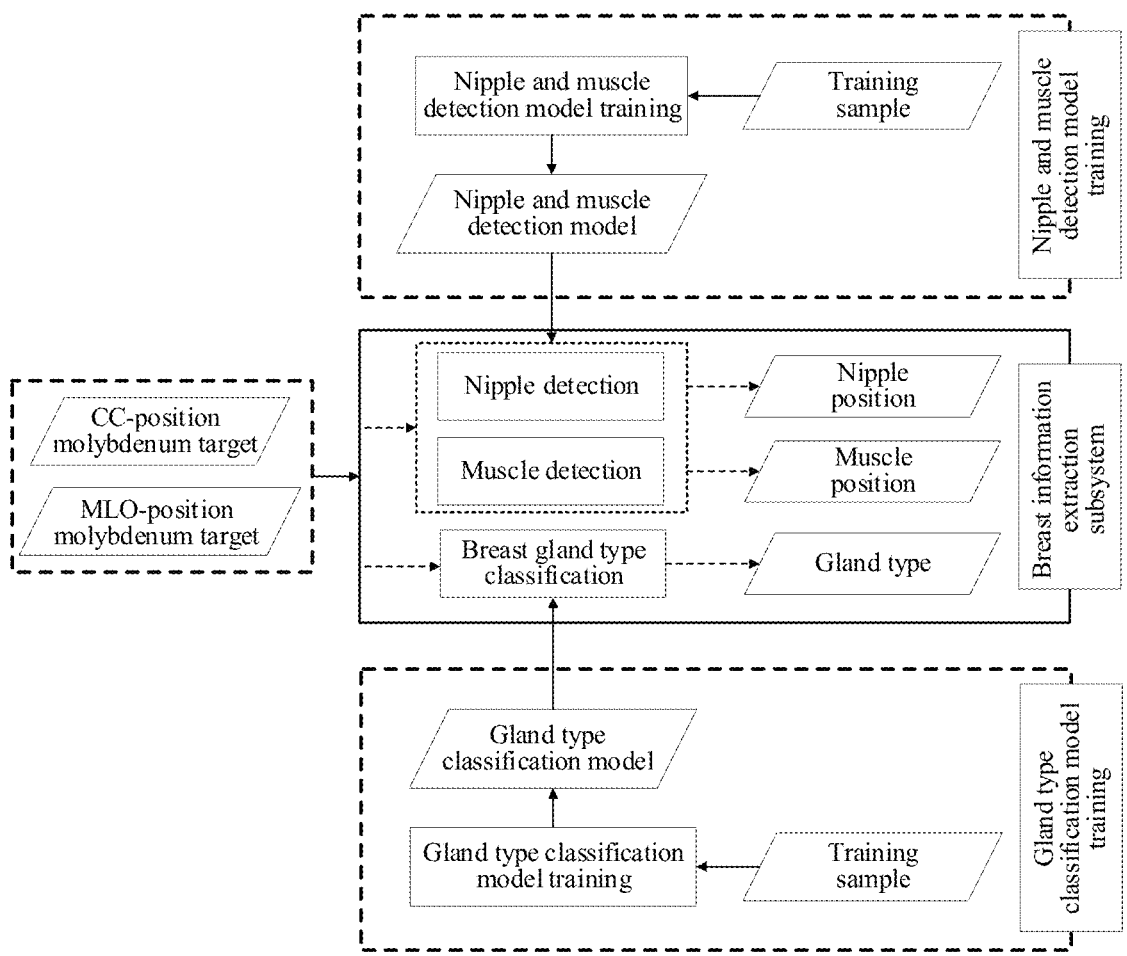
FIG. 5 is a flowchart of a breast information extraction subsystem according to another exemplary embodiment of this application.

The breast information extraction subsystem includes: a nipple detection model, a muscle detection model, and a gland type classification model. The nipple detection model and the muscle detection model can be designed as the same detection model, i.e., a nipple and muscle detection model, as shown in FIG. 5.

In some embodiments, the nipple detection model is a two-class (nipple+background) model based on Fully Convolutional Networks (FCNs). The muscle detection model is a two-class (muscle+background) model based on FCNs. The nipple and muscle detection model is a three-class (nipple+muscle+background) model based on FCNs.

Figure 3:
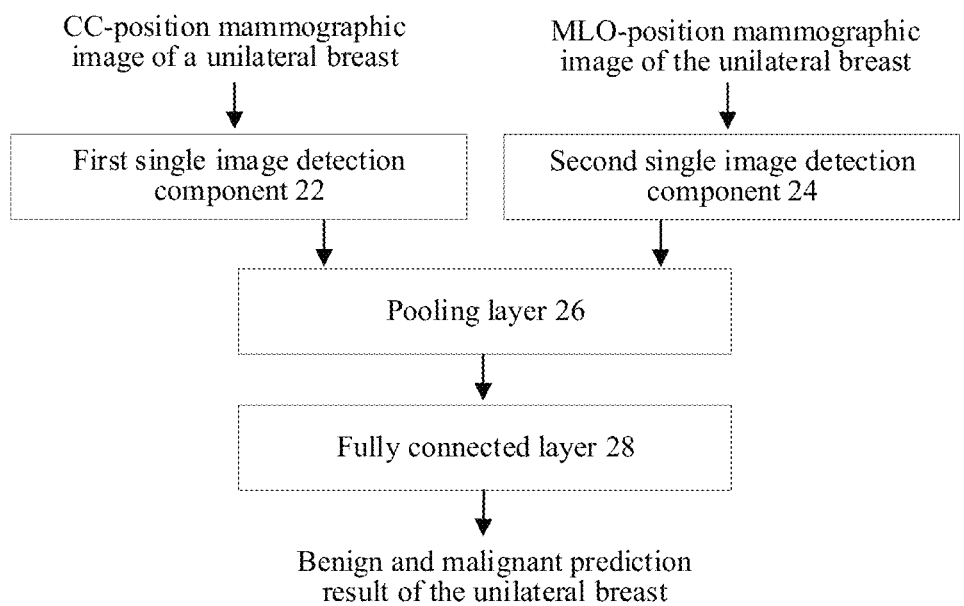
FIG. 3 is a structural block diagram of a breast benign and malignant model according to an exemplary embodiment of this application.

In some embodiments based on any one of FIG. 2 to FIG. 4, the method further includes the following steps:

A computer device invokes the nipple detection model (or the nipple and muscle detection model) to recognize a nipple position in the mammographic image. The nipple detection model is configured to calibrate each pixel in the mammographic image. The type of each pixel may be either nipple or background.

The computer device invokes the muscle detection model (or the nipple and muscle detection model) to recognize a muscle position in the mammographic image. The muscle detection model is configured to calibrate each pixel in the mammographic image. The type of each pixel may be either muscle or background.

The computer device invokes the nipple and muscle detection model to recognize the nipple position and the muscle position in the mammographic image. The nipple and muscle detection model is configured to calibrate each pixel in the mammographic image. The type of each pixel may be any one of nipple, muscle, and background.

For the CC-position mammographic image, the nipple and muscle detection model is configured to detection a nipple area. For the MLO-position mammographic image, the nipple and muscle detection model is configured to detect a nipple and muscle area.

Figure 6:
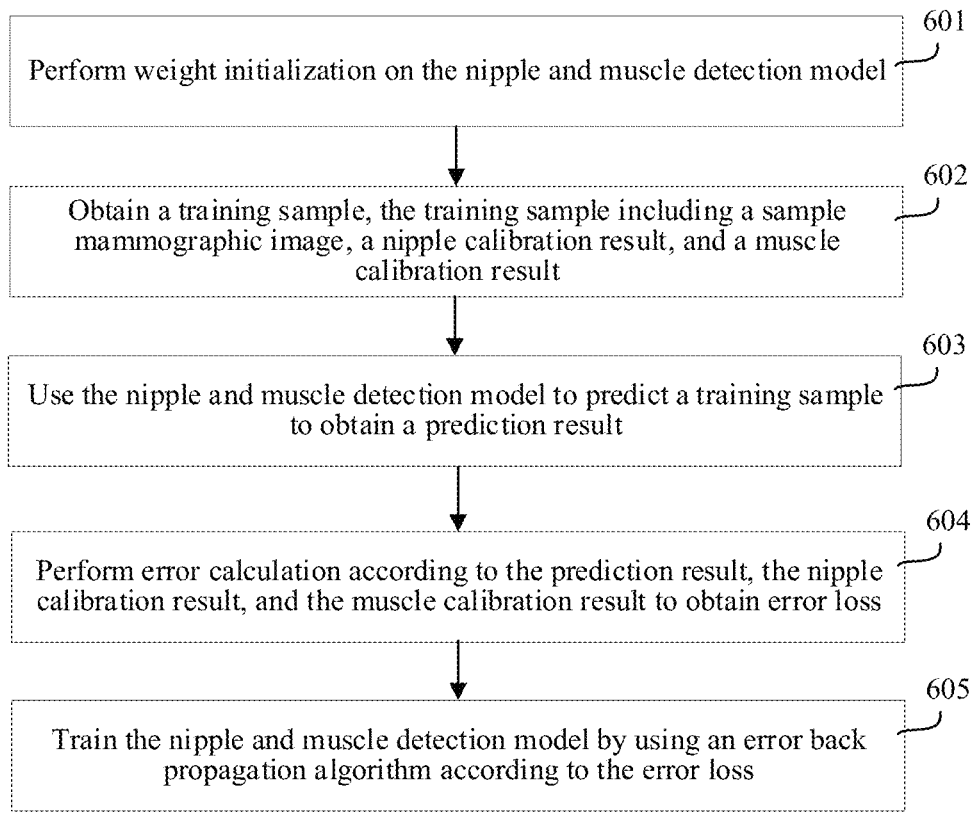
FIG. 6 is a flowchart of a method for training a nipple and muscle detection model according to another exemplary embodiment of this application.

A method for training the foregoing nipple and muscle detection model may be as follows, as shown in FIG. 6:

Step 601: perform weight initialization on the nipple and muscle detection model.

In some embodiments, the computer device may construct the nipple and muscle detection model by using an FCN model released by UC Berkeley, and perform weight initialization on the nipple and muscle detection model by a partitioned data set (pattern analysis, statistical modeling and computational learning visual object classes, PASCAL VOC). The PASCAL VOC data set is a standardized image data set for object type recognition, and may be alternatively a public tool set for accessing data sets and annotations.

Step 602: obtain a training sample, the training sample including a sample mammographic image, a nipple calibration result, and a muscle calibration result.

In some embodiments, the training sample includes two parts: a medical mammographic image public data set (digital database for screening mammography, DDSM) database and a manually calibrated data set. The manually calibrated data set may be sample mammographic images (1000+) after hiring experts for pixel level standardization using domestic hospital data. In some embodiments, for the manually calibrated data set, data enhancement may also be performed using an image flipping and/or image cropping technology.

The DDSM database is a database established by a medical institution to store breast cancer images. The DDSM database stores data types such as a malignant type, a conventional type, and a benign type. At present, many studies on the breast cancer are based on the DDSM database.

For a first training process, the sample mammographic images in the public data set DDSM can be used for training. The training process then uses the manually calibrated data set for transfer learning. Transfer learning parameters may be that the input size of the sample mammographic image is 800*800 pixels, the batch size is 8, the learning rate is 0.00001, and the maximum number of iterations is 10000).

The transfer learning is to transfer trained model parameters to a new model, to facilitate the training of a new model. Considering that most of the data or tasks are related, the learned model parameters may be shared with the new model in a manner of the transfer learning, accelerating and optimizing the learning efficiency of the model without learning from scratch like most networks. In this application, the network model data training is performed in a manner of parameter migration, and a model trained by using a task A can be configured to initialize model parameters of a task B, so that the task B can learn training convergence faster.

Step 603: use the nipple and muscle detection model to predict a training sample to obtain a prediction result.

Step 604: perform error calculation according to the prediction result, the nipple calibration result, and the muscle calibration result to obtain error loss.

Step 605: train the nipple and muscle detection model by using an error back propagation algorithm according to the error loss.

When the number of training times reaches a preset number, or the error loss is less than a threshold, it is considered that a training end condition is satisfied. A fully convolutional segmentation network for extracting the nipple area and the muscle area is obtained by training.

The gland type classification model may be a classification model constructed using the Inception V3 model released by Google. The gland type includes any one of a fat type, a small gland quantity type, a large gland quantity type, and a dense type. The Inception V3 model is one of a convolutional neural network. The convolutional neural network is a feed-forward neural network, and an artificial neuron may correspond to a surrounding unit and may perform large-scale image processing. The convolutional neural network includes a convolutional layer and a pooling layer. The Inception V3 model increases a width of a single convolutional layer, that is, convolutional kernels with different scales are used on the single convolutional layer, to optimize the network. The Inception V3 model approximates the optimal local sparse nodes through intensive components, so that computing resource is effectively used, and more features can be extracted in the same calculation amount, improving a training result. The Inception V3 model has two characteristics: one is to use 1×1 convolution for increasing and decreasing a dimension; and the other is to perform convolution and re-aggregation on a plurality of sizes at the same time.

The convolutional layer is formed by several convolutional units, and a parameter of each convolutional unit is optimized by using a back-propagation algorithm. An objective of an image convolution operation is to extract different features of inputted images. A first convolutional layer may merely extract some lower-level features such as edges, lines, and angles. However, more layers of networks can iteratively extract more complex features from the low-level features.

Figure 7:
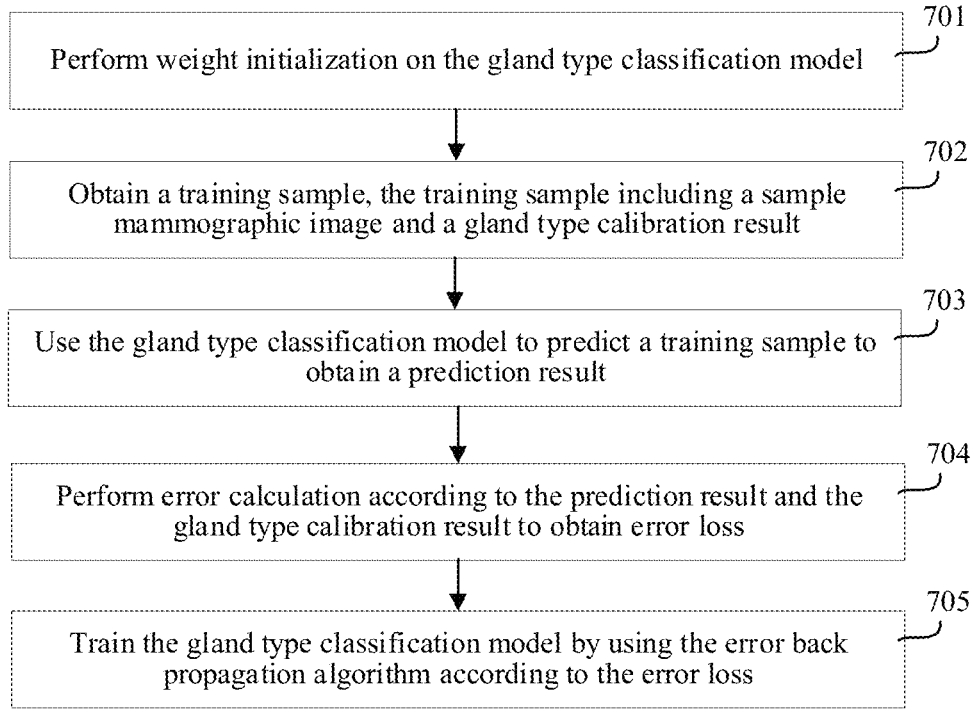
FIG. 7 is a flowchart of a method for training a gland type classification model according to another exemplary embodiment of this application.

A method for training the foregoing gland type classification model may be as follows, as shown in FIG. 7:

Step 701: perform weight initialization on the gland type classification model.

In some embodiments, the computer device may construct the gland type classification model by using the Inception V3 model released by Google, and the outputted classification categories are set to 4. Subsequently, weight initialization is performed using an ImageNet (computer vision standard data set) data set.

Step 702: obtain a training sample, the training sample including a sample mammographic image and a gland type calibration result.

In some embodiments, the training sample includes two parts: a public data set DDSM released by Google and a manually calibrated data set. The manually calibrated data set may be sample mammographic images (1000+) after hiring experts for gland type calibration using domestic hospital data. In some embodiments, for the manually calibrated data set, data enhancement may also be performed using an image flipping and/or image cropping technology.

For a first training process, the sample mammographic images in the public data set DDSM can be used for training. The first training process then uses the manually calibrated data set for transfer learning. Transfer learning parameters may be that: an error back propagation algorithm uses Root Mean Square prop (RMSprop), the batch size is 64, the initial learning rate is 0.00001, and the maximum number of iterations is 10,000.

Step 703: use the gland type classification model to predict a training sample to obtain a prediction result.

Step 704: perform error calculation according to the prediction result and the gland type calibration result to obtain error loss.

Step 705: train the gland type classification model by using the error back propagation algorithm according to the error loss.

When the number of training times reaches a preset number, or the error loss is less than a threshold, it is considered that a training end condition is satisfied. An attribute classification network for gland type recognition is obtained by training.

For a Lesion Recognition Subsystem

Figure 8:
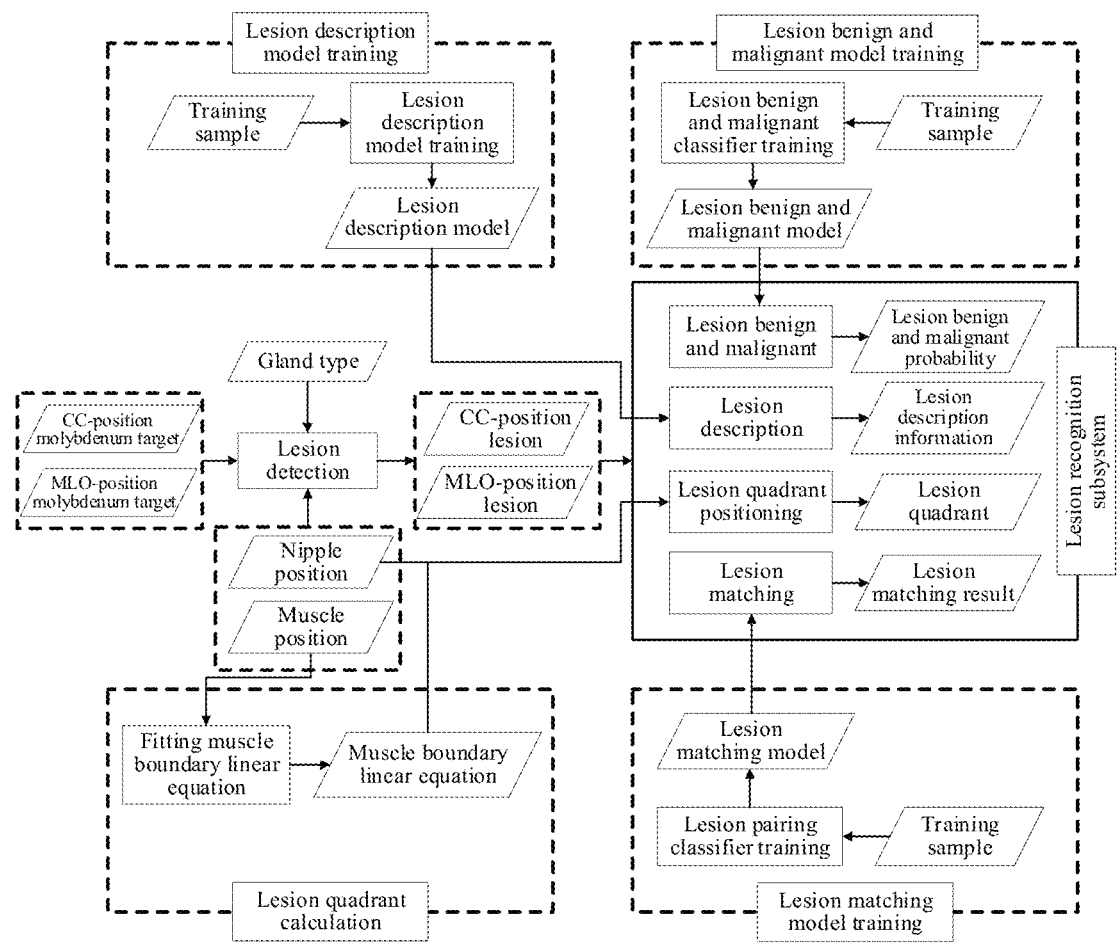
FIG. 8 is a functional diagram of a lesion detection subsystem according to another exemplary embodiment of this application.

The lesion recognition subsystem includes a lesion description model, a lesion benign and malignant model, a lesion matching model, and a lesion quadrant positioning model, as shown in FIG. 8.

In some embodiments based on FIG. 2 to FIG. 4, the method further includes at least one of the following four steps:

The computer device invokes the lesion description model to detect a lesion in the mammographic image to obtain lesion description information.

The computer device invokes the lesion benign and malignant model to perform benign and malignant recognition on the lesion in the mammographic image to obtain a lesion benign and malignant probability.

The computer device invokes the lesion matching model to determine the consistency of lesions of the CC-position mammographic image and the MLO-position mammographic image, to obtain a lesion matching probability.

The computer device invokes the lesion quadrant positioning model to perform quadrant calculation on the lesion in the mammographic image.

Figure 9:
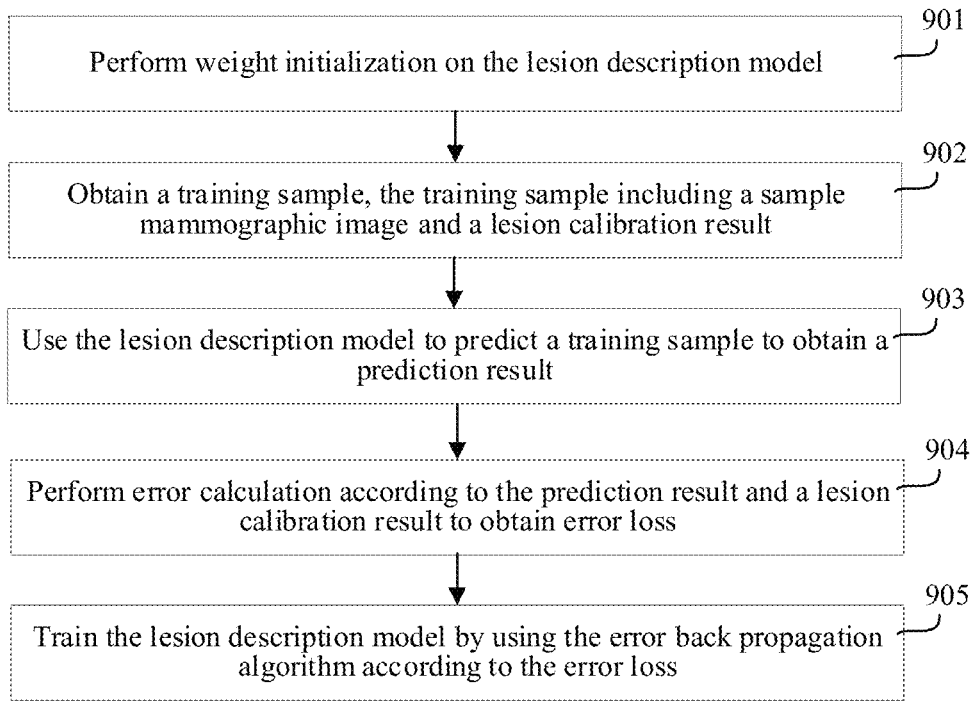
FIG. 9 is a flowchart of a method for training a lesion description model according to an exemplary embodiment of this application.

The lesion description model may be a classification model constructed using the Inception V3 model released by Google. A method for training the foregoing lesion description model may be as follows, as shown in FIG. 9:

Step 901: perform weight initialization on the lesion description model.

In some embodiments, the lesion description model is constructed using the Inception V3 model released by Google. In some embodiments, the last fully connected layer of the Inception V3 model is modified to multiple parallel fully connected layers that support simultaneous training of multiple tasks. The output category corresponding to each task is set to 2, that is, each task shares all parameters other than the last fully connected layer. Subsequently, weight initialization is performed using the ImageNet data set.

Step 902: obtain a training sample, the training sample including a sample mammographic image and a lesion calibration result.

In some embodiments, the training sample includes two parts: a public data set DDSM released by Google and a manually calibrated data set. The manually calibrated data set may be sample mammographic images (1000+) after hiring experts for lesion attribute calibration using domestic hospital data. Taking lump attributes as an example, each lump is labeled with at least one piece of description information in round or irregular shape, a clear or fuzzy boundary, phyllodes or no phyllodes appearing on the boundary, and burr or no burr appearing on the boundary. In some embodiments, for the manually calibrated data set, data enhancement may also be performed using an image flipping and/or image cropping technology.

For a first training process, the sample mammographic images in the public data set DDSM can be used for training. The training process then uses the manually calibrated data set for transfer learning. Transfer learning parameters may be that: an error back propagation algorithm uses Adam, the batch size is 64, the initial learning rate is 0.001, and the maximum number of iterations is 10,000.

Step 903: use the lesion description model to predict a training sample to obtain a prediction result.

Step 904: perform error calculation according to the prediction result and a lesion calibration result to obtain error loss.

Step 905: train the lesion description model by using the error back propagation algorithm according to the error loss.

When the number of training times reaches a preset number, or the error loss is less than a threshold, it is considered that a training end condition is satisfied. An attribute classification network for lesion recognition is obtained by training.

Figure 10:
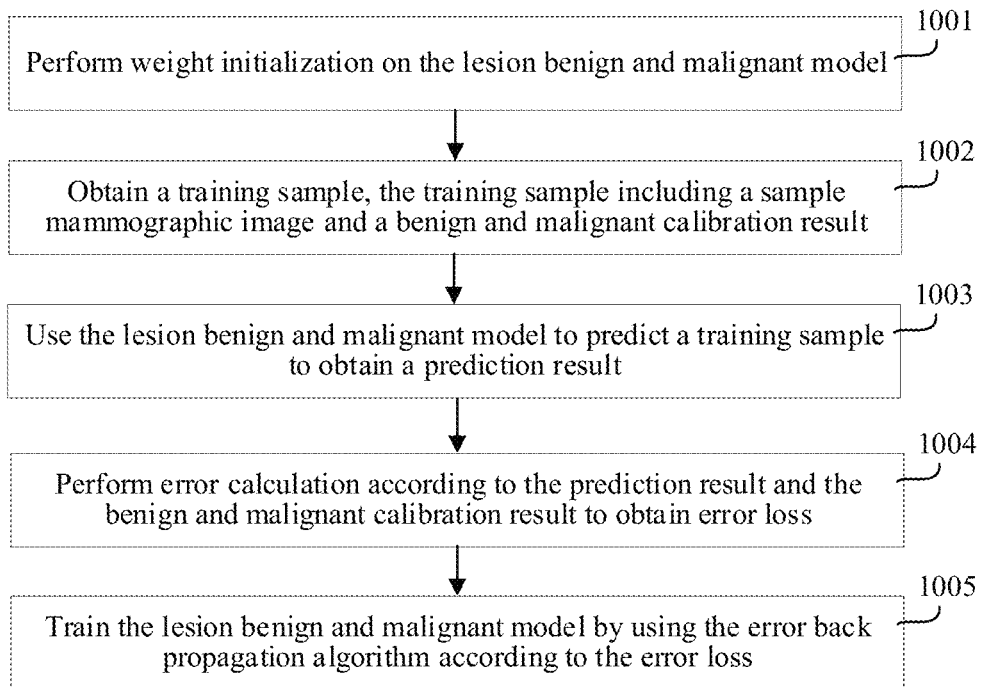
FIG. 10 is a flowchart of a method for training a lesion benign and malignant model according to an exemplary embodiment of this application.

The lesion benign and malignant model may be a classification model constructed using the Inception V3 model released by Google. A method for training the foregoing lesion benign and malignant model may be as follows, as shown in FIG. 10:

Step 1001: perform weight initialization on the lesion benign and malignant model.

In some embodiments, the lesion benign and malignant model is constructed using the Inception V3 model released by Google. In some embodiments, the last pooling layer of the Inception V3 model is modified to a max pooling layer, and the number of output categories is set to 2. Subsequently, weight initialization is performed using the ImageNet data set.

Step 1002: obtain a training sample, the training sample including a sample mammographic image and a benign and malignant calibration result.

In some embodiments, the training sample includes two parts: a public data set DDSM released by Google and a manually calibrated data set. The manually calibrated data set may be sample mammographic images (16,000+) after hiring experts for lesion benign and malignant calibration using domestic hospital data. The benign and malignant calibration result includes: malignant calcified lesions and malignant lump lesions are positive samples, and benign calcified lesions, benign lump lesions, and normal areas are negative samples. In some embodiments, for the manually calibrated data set, data enhancement may also be performed using an image flipping and/or image cropping technology.

For a first training process, the sample mammographic images in the public data set DDSM can be used for training. The training process then uses the manually calibrated data set for transfer learning. Transfer learning parameters may be that: an error back propagation algorithm uses Adam, the batch size is 64, the initial learning rate is 0.001, and the maximum number of iterations is 10,000.

Step 1003: use the lesion benign and malignant model to predict a training sample to obtain a prediction result.

Step 1004: perform error calculation according to the prediction result and a lesion calibration result to obtain error loss.

Step 1005: train the lesion benign and malignant model by using the error back propagation algorithm according to the error loss.

When the number of training times reaches a preset number (such as 10,000), or the error loss is less than a threshold, it is considered that a training end condition is satisfied. An attribute classification network for lesion recognition is obtained by training. In some embodiments, a probability of greater than 0.5 is considered to be suspected of containing malignant lesions.

The lesion quadrant positioning model is a model based on a muscle straight linear fitting equation. A muscle boundary linear equation is obtained by linearly fitting the boundary of the muscle position in the mammographic image. Quadrant calculation is performed on the lesions in the mammographic image according to the nipple position.

The computer device obtains the lesion quadrant positioning model. The lesion quadrant positioning model is obtained by training multiple sample images. Each pixel in the sample images is labeled. The labeling types include: background, nipple and muscle. In other words, the lesion quadrant positioning model can recognize that each pixel in an image belongs to either the background, the nipple or the muscle. The computer device inputs the CC-position mammographic image into the lesion quadrant positioning model, and the nipple position of the CC-position mammographic image (the CC-position mammographic image has no muscle information, and therefore has no muscle area) can be determined based on the lesion quadrant positioning model. The computer device inputs the MLO-position mammographic image into the lesion quadrant positioning model, and the nipple position and the muscle position in the MLO-position mammographic image can be determined based on the lesion quadrant positioning model. For the CC-position mammographic image, the computer device determines a first division line according to the nipple and a breast edge boundary line, and determines that a first lesion area is located in an inner quadrant or an outer quadrant according to the first division line. For the MLO-position mammographic image, the computer device fits the muscle boundary linear equation according to the muscle position so as to determine a muscle boundary line (i.e., the object boundary line in the above), then determines a second division line according to the nipple position and the muscle boundary line, and determines that a second lesion area is located in an upper quadrant or a lower quadrant according to the second division line.

Figure 11:
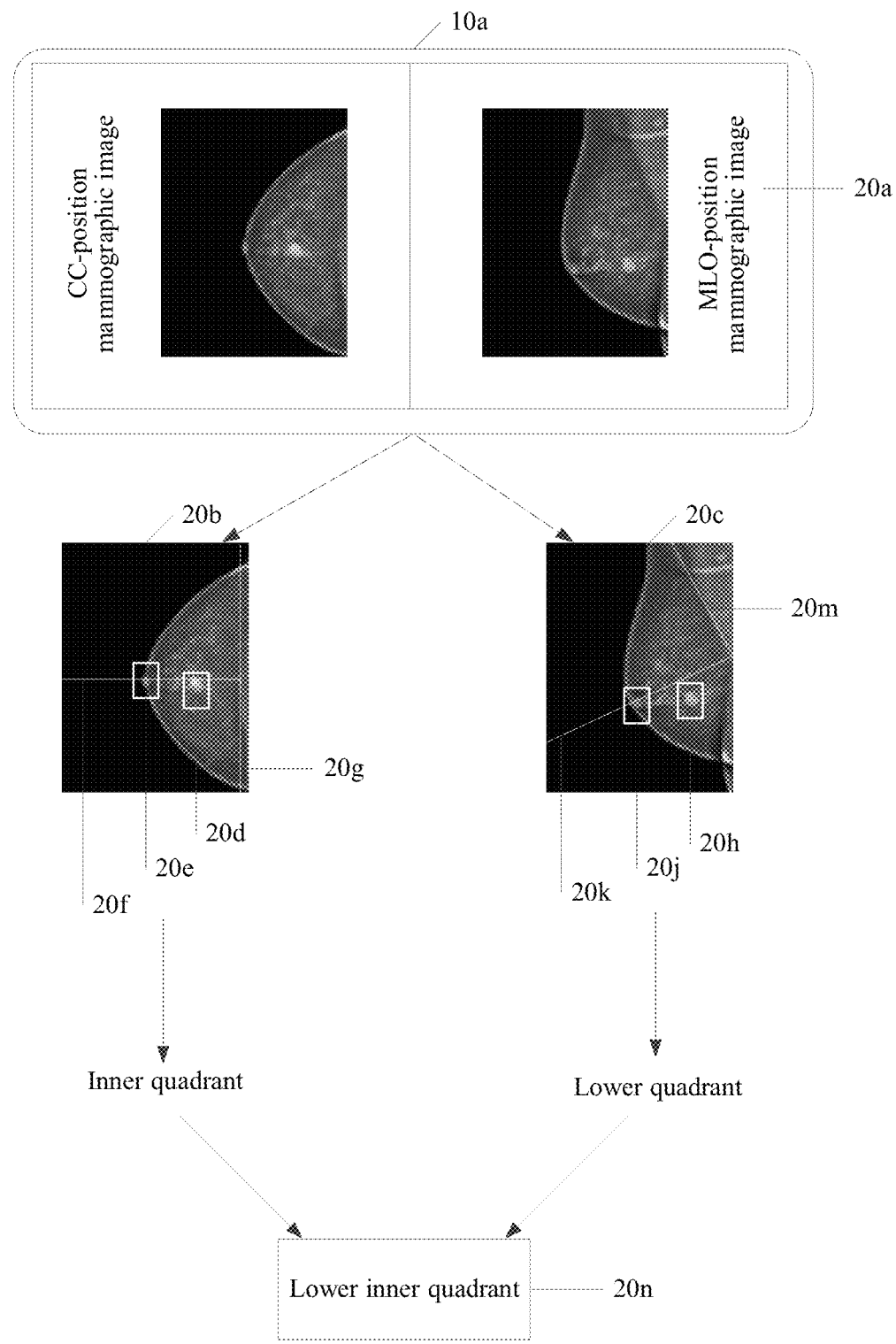
FIG. 11 is a schematic diagram showing the positioning of a lesion quadrant positioning model according to an exemplary embodiment of this application.

As shown in the user interface 20*a* shown in FIG. 11, a computer device 10*a* obtains a mammographic image of the same breast of the same patient, and displays the obtained mammographic image on a screen. The mammographic image includes: a CC-position mammographic image 20*b* and an MLO-position mammographic image 20*c*. The CC-position mammographic image is obtained by imaging the breast at a cranial-caudal position, and the MLO-position mammographic image is obtained by imaging the breast at a mediolateral-oblique position.

The computer device 10*a* obtains a lump detection model and a calcification detection model (i.e., the lesion description model in this application). The lump detection model can recognize a position area where a lump lesion in the image is located. The calcification detection model can recognize a position area where a calcified lesion in the image is located. A lump category and a calcification category are lesion categories.

For the lump detection model, the computer device 10*a* can input the CC-position mammographic image 20*b* into the lump detection model, so that the lump detection model can output a lesion area 20*d* in the CC-position mammographic image 20*b* where a lesion object in the CC-position mammographic image 20*b* is located, and may also determine that the lesion category of the lesion object in the CC-position mammographic image 20*b* is the lump category.

The computer device 10*a* can input the MLO-position mammographic image 20*c* into the lump detection model, so that the lump detection model can also output a lesion area 20*h* in the MLO-position mammographic image 20*c* where a lesion object in the MOL-position mammographic image 20*c* is located, and may also determine that the lesion category of the lesion object in the MLO-position mammographic image 20*c* is the lump category.

For the calcification detection model, the computer device 10*a* also inputs the CC-position mammographic image 20*b* into the calcification detection model, and the calcification detection model does not detect a calcified lesion in the CC-position mammographic image 20*b*. The computer device 10*a* also inputs the MLO-position mammographic image 20*c* into the calcification detection model, and the calcification detection model likewise does not detect a calcified lesion in the MLO-position mammographic image 20*c*.

Therefore, for the CC-position mammographic image 20*b* and the MLO-position mammographic image 20*c*, there is only a lump lesion, and the lump lesion is located in the lesion area 20*d* in the CC-position mammographic image 20*b*. The lump lesion is located in the lesion area 20*h* in the MLO-position mammographic image 20*c*.

The computer device 10*a* obtains the lesion quadrant positioning model. The lesion quadrant positioning model can recognize the issue category of each pixel in the image. Tissue categories include a nipple category, a muscle category, and a background category.

The computer device 10a inputs the CC-position mammographic image 20b into the lesion quadrant positioning model, so that the model can determine the issue category of each pixel in the CC-position mammographic image 20b. In the CC-position mammographic image 20b, the computer device 10a combines pixels belonging to the nipple category into an area 20e, and the area 20e is an area where the nipple is located. The computer device 10a determines a breast edge line 20g in the CC-position mammographic image 20b, and uses a line 20f that is perpendicular to the breast edge line 20g and passes through the area 20e as a quadrant division line 20f. In the CC-position mammographic image 20b, the inner quadrant is located below the quadrant division line 20f, and the outer quadrant is located above the quadrant division line 20f. In the CC-position mammographic image 20b, since the lesion area 20d is located in the inner quadrant (most of the lesion area 20d is located in the inner quadrant, thus it is considered that the lesion area 20d is located in the inner quadrant), the computer device 10a can determine that the lump lesion in the CC-position mammographic image 20b is located in the inner quadrant.

The computer device 10a inputs the MLO-position mammographic image 20c into the lesion quadrant positioning model, so that the model can determine the issue category of each pixel in the MLO-position mammographic image 20c. In the MLO-position mammographic image 20c, the computer device 10a combines pixels belonging to the nipple category into an area 20j, and the area 20j is an area where the nipple is located. The computer device 10a combines quadrants belonging to the muscle category into a muscle area, and determines an area boundary line 20m between the muscle area and a non-muscle area, and uses a line 20k that is perpendicular to the area boundary line 20m and passes through the area 20j as a quadrant division line 20k. In the MLO-position mammographic image 20c, the lower quadrant is located below the quadrant division line 20k, and the upper quadrant is located above the quadrant division line 20k. In the MLO-position mammographic image 20c, since the lesion area 20h is located in the lower quadrant, the computer device 10a can determine that the lump lesion in the MLO-position mammographic image 20c is located in the lower quadrant.

The computer device 10a combines the inner quadrant determined by the CC-position mammographic image 20b and the lower quadrant determined by the MLO-position mammographic image 20c into quadrant position information 20n "lower inner quadrant".

The computer device 10a can combine the quadrant position information 20n "lower inner quadrant" and a lesion category "mass" corresponding to both the CC-position mammographic image 20b and the MLO-position mammographic image 20c into a diagnostic opinion: "a lump appearing in the lower inner quadrant".

Figure 12:
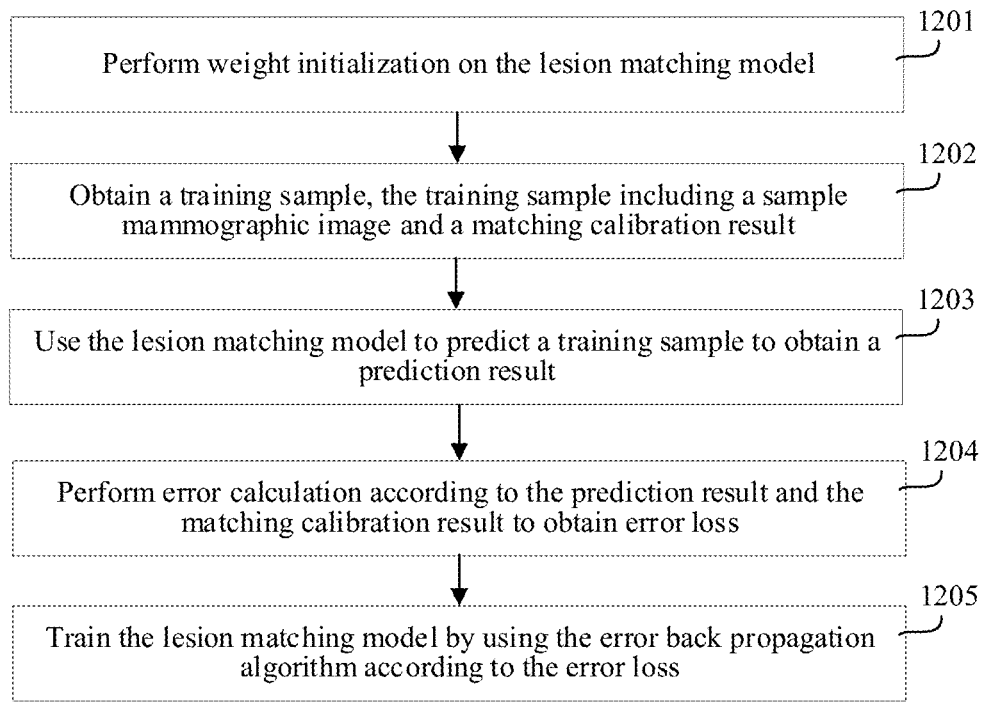
FIG. 12 is a flowchart of a method for training a lesion matching model according to an exemplary embodiment of this application.

The lesion matching model may be a classification model constructed based on the VGG model released by the University of Oxford. A training process of the lesion matching model may be as follows, as shown in FIG. 12:

Step 1201: perform weight initialization on the lesion matching model.

In some embodiments, the lesion matching model is constructed using the VGG model released by the University of Oxford. In some embodiments, pool 5 layer results of the VGG model are taken for fusion, and subsequently, consistent with the original VGG, three fully connected layers are adopted to obtain a result that the number of categories is 2. Subsequently, weight initialization is performed using the ImageNet data set.

Step 1202: obtain a training sample, the training sample including a sample mammographic image and a matching calibration result.

In some embodiments, the training sample includes two parts: a public data set DDSM released by Google and a manually calibrated data set. The manually calibrated data set may be sample mammographic images (1000+) obtained by hiring experts to take a pair of plaques in the CC-position mammographic image and the MLO-position mammographic image representing the same lesion as a positive sample and any another pair of plaques not representing the same lesion as a negative sample by using domestic hospital data. In some embodiments, for the manually calibrated data set, data enhancement may also be performed using an image flipping and/or image cropping technology.

For a first training process, the sample mammographic images in the public data set DDSM can be used for training. The training process then uses the manually calibrated data set for transfer learning. Transfer learning parameters may be that: an error back propagation algorithm uses Adam, the batch size is 128, the initial learning rate is 0.001, and the maximum number of iterations is 10,000.

Step 1203: use the lesion matching model to predict a training sample to obtain a prediction result.

Step 1204: perform error calculation according to the prediction result and the matching calibration result to obtain error loss.

Step 1205: train the lesion matching model by using the error back propagation algorithm according to the error loss.

When the number of training times reaches a preset number (such as 10,000), or the error loss is less than a threshold, it is considered that a training end condition is satisfied. An attribute classification network for recognizing the matching degree of lesions is obtained by training. In some embodiments, in a prediction phase, a first lesion in the CC-position mammographic image and a second lesion in the MLO-position mammographic image are inputted at the same time to obtain the probability of whether the first lesion and the second lesion are the same lesion.

For a Breast Benign and Malignant Subsystem

Figure 13:
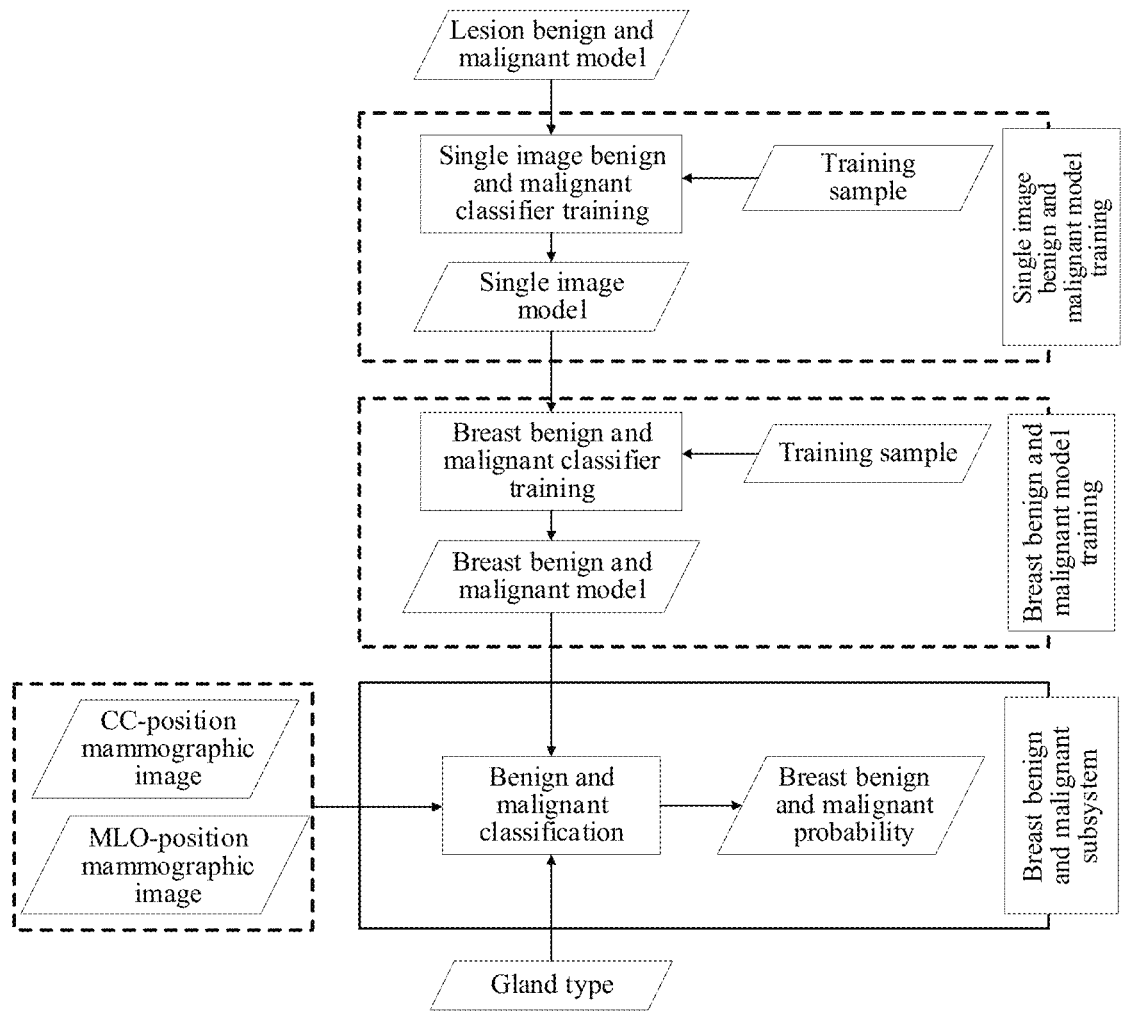
FIG. 13 is a functional diagram of a breast benign and malignant model according to an exemplary embodiment of this application.
Figure 14:
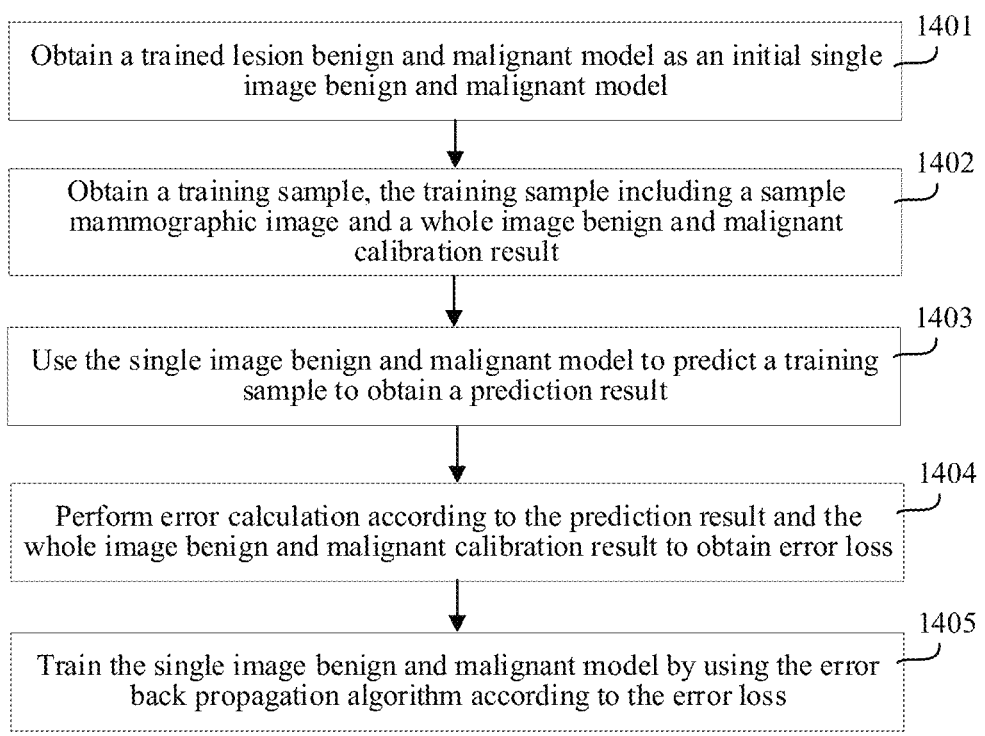
FIG. 14 is a flowchart of a method for training a single image benign and malignant model according to an exemplary embodiment of this application.

The breast benign and malignant subsystem includes a breast benign and malignant model, as shown in FIG. 13. The breast benign and malignant model is configured to perform benign and malignant detection on a CC-position mammographic image and an MLO-position mammographic image of a unilateral breast, to obtain a benign and malignant probability of the unilateral breast. The structure of the breast benign and malignant model is shown in FIG. 3.

In some embodiments based on FIG. 2 to FIG. 4, a training process of the foregoing breast benign and malignant model includes: training of a single image benign and malignant model, and training of the breast benign and malignant model. The single image benign and malignant model is configured to construct a first single image detection component 22 and a second single image detection component 24 in FIG. 3.

A method for training the single image benign and malignant model may include the following steps:

Step 1401: obtain a trained lesion benign and malignant model as an initial single image benign and malignant model.

Step 1402: obtain a training sample, the training sample including a sample mammographic image and a whole image benign and malignant calibration result.

In some embodiments, the training sample includes two parts: a public data set DDSM released by Google and a manually calibrated data set. The manually calibrated data set may be (16,000+) sample mammographic images after hiring experts for whole image benign and malignant calibration using domestic hospital data. The whole image benign and malignant calibration result includes: using a malignant mammographic image as a positive sample, and a mammographic image of which the whole image is a benign and/or normal as a negative sample. In some embodiments, for the manually calibrated data set, data enhancement can also be performed using an image flipping and/or image cropping technology.

Transfer learning is performed on the initial single image benign and malignant model by using the manually calibrated data set Transfer learning parameters may be that: an error back propagation algorithm uses Adam, the batch size is 64, the initial learning rate is 0.001, and the maximum number of iterations is 10,000.

Step 1403: use the single image benign and malignant model to predict a training sample to obtain a prediction result.

Step 1404: perform error calculation according to the prediction result and the whole image benign and malignant calibration result to obtain error loss.

Step 1405: train the single image benign and malignant model by using the error back propagation algorithm according to the error loss.

When the number of training times reaches a preset number (such as 10,000), or the error loss is less than a threshold, it is considered that a training end condition is satisfied. An attribute classification network for single image benign and malignant recognition is obtained by training. In some embodiments, a probability of greater than 0.5 is considered to be suspected of containing malignant lesions.

Two trained single image benign and malignant models are respectively used as the first single image detection component 22 and the second single image detection component 24, so that the breast benign and malignant model is formed by adding a pooling layer 25 and a fully connected layer 28 to keep the output categories of the model at 2.

The training sample of the single image benign and malignant model is used as a new training sample. After data enhancement (since the images are mammographic images, data enhancement of flipping and cropping is mainly performed, and there is no need to perform data enhancement of color space), the single image benign and malignant model is extended to a CC and MLO dual-image benign and malignant classification model. Training parameters may be that: (a descent algorithm uses RMSprop, the batch size is 32, the initial learning rate is 0.01, and the maximum number of iterations is 10,000).

For an Automatic Report Generation Subsystem

Figure 15A:
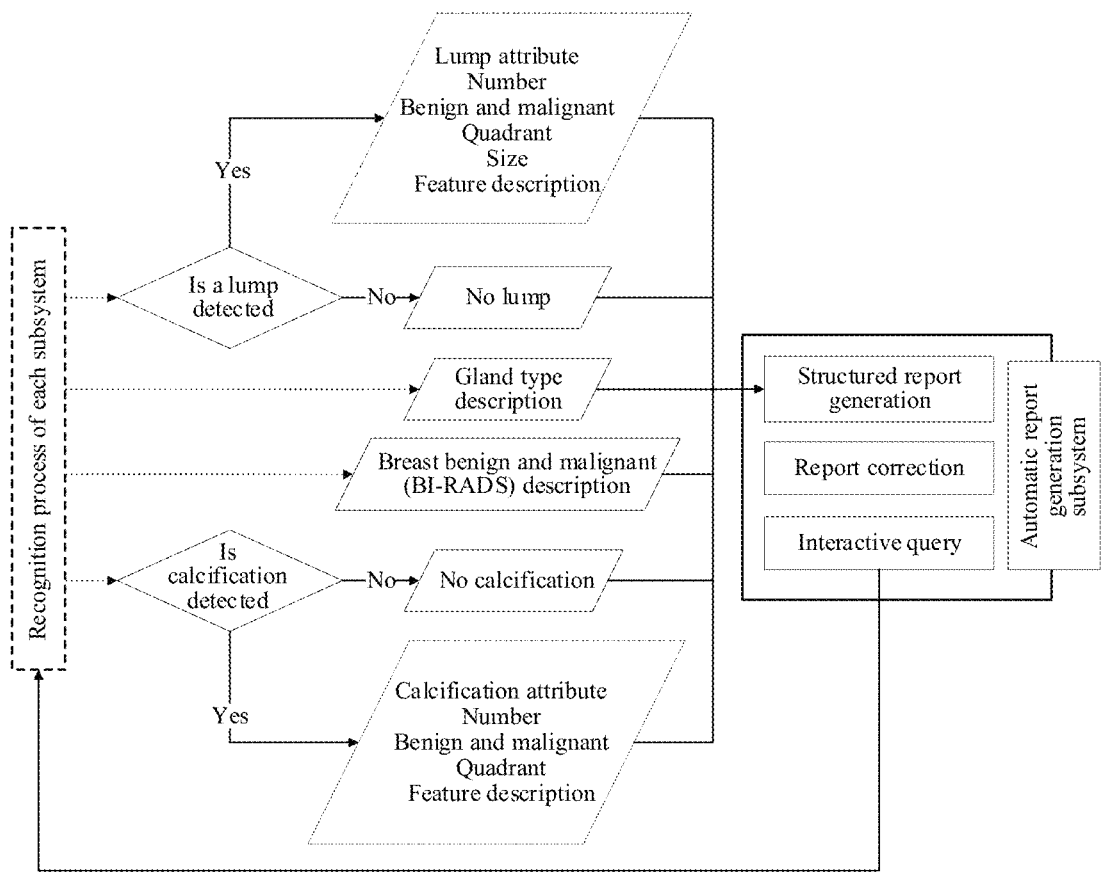
FIG. 15(A) is a functional diagram of an automatic reporting subsystem according to another exemplary embodiment of this application.
Figure 15B:
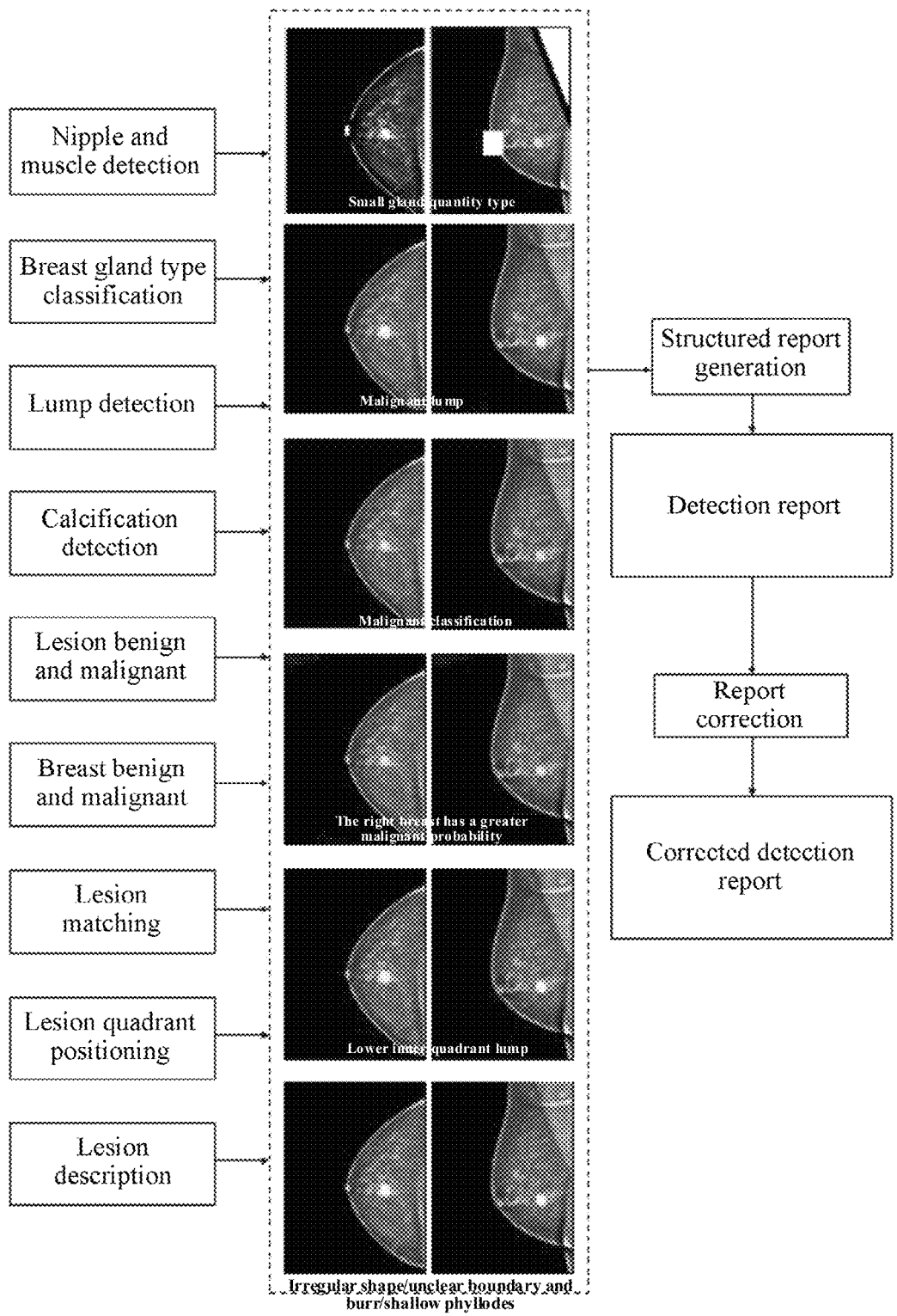
FIG. 15(B) is a schematic diagram showing the reporting of a structured report according to an exemplary embodiment of this application.

FIG. 15(A) is a schematic diagram of fusing the results of the foregoing subsystems by the automatic report generation subsystem to generate a structured report. The automatic report generation subsystem fuses all the detection and recognition results of the foregoing subsystems to generate a structured report. A doctor can modify the generated report and query relevant information of an area of interest through interactive query. Details of steps are described below:

The automatic report generation subsystem has the following functions:

Generation of a structured detection report:

A computer device summarizes the detection and recognition results obtained by all the foregoing subsystems to automatically generate report content of the detection report described in the BI-RADS standard. The report content of the detection report includes: lump description, calcification description, gland type description, and breast benign and malignant description, etc. In some embodiments, the detection report may refer to FIG. 15(B). The detection report includes: a small gland quantity type, a malignant lump, malignant calcification, the right breast having a greater malignant probability, a lower inner quadrant lump, and lump description information, etc. The lump description information includes: at least one of irregular shape, unclear boundary, burr, and shallow phyllodes.

Correction of the Detection Report:

The doctor can revise the detection and recognition result of this system and the automatically generated report through review or other methods to obtain a diagnosis report. The computer device receives a report correction request sent by a doctor device, and corrects the detection report according to the report correction request.

Interactive Query:

The doctor can query information of interest in an interactive manner. For example, the doctor can select an area of interest in a mammographic image, and invoke a lesion benign and malignant classification model of this system to obtain a benign and malignant result of this area. The computer device also receives a local query request that is used for requesting to query a local area in the mammographic image, and outputs a detection report corresponding to the local area according to the local query request.

Figure 16:
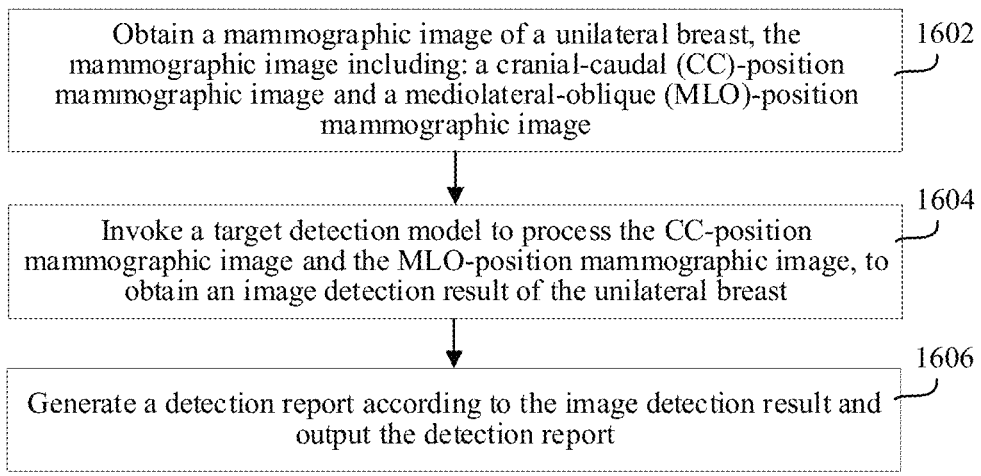
FIG. 16 is a schematic flowchart of a mammographic image processing method according to an exemplary embodiment of this application.

Referring to FIG. 16, this application further provides a mammographic image processing method, which is executed by a computer device. The mammographic image processing method includes the following steps:

Step 1602: obtain a mammographic image of a unilateral breast, the mammographic image including: a cranial-caudal (CC)-position mammographic image and a mediolateral-oblique (MLO)-position mammographic image.

Step 1604: invoke a target detection model to process the CC-position mammographic image and the MLO-position mammographic image, to obtain an image detection result of the unilateral breast.

Step 1606: generate a detection report according to the image detection result and output the detection report.

In some embodiments, the target detection model includes: a first single image detection component, a second single image detection component, a pooling layer, and a fully connected layer. The step of invoking a target detection model to process the CC-position mammographic image and the MLO-position mammographic image, to obtain an image detection result of the unilateral breast specifically includes: invoking the first single image detection component to process the CC-position mammographic image to obtain a first feature; invoking the second single image detection component to process the MLO-position mammographic image to obtain a second feature; and inputting the first feature and the second feature into the pooling layer and the fully connected layer to obtain the image detection result of the unilateral breast.

In some embodiments, before the invoking a target detection model to process the CC-position mammographic image and the MLO-position mammographic image, to obtain an image detection result of the unilateral breast, the mammographic image processing method further includes: invoking a gland type classification model to recognize a gland type in the mammographic image to obtain a gland type recognition result. The step of invoking a target detection model to process the CC-position mammographic image and the MLO-position mammographic image, to obtain an image detection result of the unilateral breast specifically includes: determining a prediction threshold corresponding to the target detection model according to the gland type recognition result; and invoking the target detection model after determining the prediction threshold to process the CC-position mammographic image and the MLO-position mammographic image, to obtain the image detection result of the unilateral breast.

In some embodiments, the step of invoking a gland type classification model to recognize a gland type in the mammographic image to obtain a gland type recognition result specifically includes: invoking the gland type classification model to recognize a gland type of the CC-position mammographic image to obtain a first gland type; invoking the gland type classification model to recognize a gland type of the MLO-position mammographic image to obtain a second gland type; and determining the first gland type or the second gland type which has a greater gland density as a gland type of the unilateral breast.

In some embodiments, the mammographic image processing method further includes: invoking an abnormality recognition model to perform abnormality detection on the mammographic image to obtain an abnormality detection result. The abnormality detection includes at least one of lump detection and calcification detection.

In some embodiments, the abnormality recognition model includes at least one of an abnormality description model, an abnormality classification model, an abnormality matching model, and an abnormality quadrant positioning model. The step of invoking an abnormality recognition model to perform abnormality detection on the mammographic image to obtain an abnormality detection result specifically includes at least one of the following steps: invoking the abnormality description model to detect an abnormality area in the mammographic image to obtain abnormality description information; invoking the abnormality classification model to recognize an abnormality category in the mammographic image to obtain a corresponding category probability; invoking the abnormality matching model to determine the consistency of abnormality areas of the CC-position mammographic image and the MLO-position mammographic image, to obtain an abnormality matching probability; and invoking the abnormality quadrant positioning model to perform quadrant calculation on the abnormality area in the mammographic image.

In some embodiments, before the invoking the abnormality quadrant positioning model to perform quadrant calculation on the abnormality area in the mammographic image, the mammographic image processing method further includes: invoking a nipple detection model to recognize a nipple position in the mammographic image. The step of invoking the abnormality quadrant positioning model to perform quadrant calculation on the abnormality area in the mammographic image specifically includes: invoking the abnormality quadrant positioning model to perform quadrant calculation on the abnormality area in the mammographic image according to the nipple position.

In some embodiments, the mammographic image processing method further includes: when the mammographic image is the MLO-position mammographic image, invoking a muscle detection model to recognize a muscle position in the mammographic image.

In some embodiments, the mammographic image processing method further includes: receiving a report correction request; and correcting the detection report according to the report correction request.

In some embodiments, the mammographic image processing method further includes: receiving a local query request, the local query request being used for requesting to query a local area in the mammographic image; and outputting a detection report corresponding to the local area according to the local query request.

For the specific implementation details of the mammographic image processing method, please refer to the description content of the mammographic image assisted diagnosis method mentioned in the foregoing embodiments. For the specific processing process of the target detection model, reference may be made to the processing process of the breast benign and malignant detection model in the mammographic image assisted diagnosis method mentioned in the foregoing embodiments. For the specific processing process of the abnormality recognition model, reference may be made to the processing process of the lesion recognition model in the mammographic image assisted diagnosis method mentioned in the foregoing embodiments. For the specific processing process of the abnormality description model, reference may be made to the processing process of the lesion description model in the mammographic image assisted diagnosis method mentioned in the foregoing embodiments. For the specific processing process of the abnormality classification model, reference may be made to the processing process of the lesion benign and malignant model in the mammographic image assisted diagnosis method mentioned in the foregoing embodiments. For the specific processing process of the abnormality matching model, reference may be made to the processing process of the lesion matching model in the mammographic image assisted diagnosis method mentioned in the foregoing embodiments. For the specific processing process of the abnormality quadrant positioning model, reference may be made to the processing process of the lesion quadrant positioning model in the mammographic image assisted diagnosis method mentioned in the foregoing embodiments.

Figure 17:
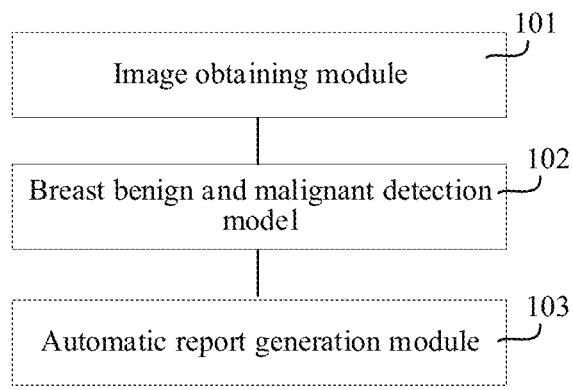
FIG. 17 is a block diagram of a mammographic image assisted diagnosis apparatus according to an exemplary embodiment of this application.

FIG. 17 is a block diagram of a mammographic image assisted diagnosis apparatus according to an exemplary embodiment of this application. The apparatus can be configured to implement the functions of the foregoing mammographic image assisted diagnosis method. The apparatus includes:

an image obtaining module 101, configured to obtain a mammographic image of a unilateral breast, the mammographic image including: a CC-position mammographic image and an MLO-position mammographic image;

a breast benign and malignant detection model 102, configured to perform benign and malignant prediction on the CC-position mammographic image and the MLO-position mammographic image, to obtain a benign and malignant prediction result of the unilateral breast; and an automatic report generation module 103, configured to generate and output a detection report, the detection report including the benign and malignant prediction result of the unilateral breast.

In some embodiments, the breast benign and malignant detection model 102 includes: a first single image detection component, a second single image detection component, a pooling layer, and a fully connected layer. The breast benign and malignant detection model 102 is configured to invoke the first single image detection component to process the CC-position mammographic image to obtain a first logits feature. The breast benign and malignant detection model 102 is configured to invoke the second single image detection component to process the MLO-position mammographic image to obtain a second logits feature. The breast benign and malignant detection model 102 is configured to input the first logits feature and the second logits feature into the pooling layer and the fully connected layer to obtain the benign and malignant prediction result of the unilateral breast.

In some embodiments, the mammographic image assisted diagnosis apparatus further includes a gland type classification model. The gland type classification model is configured to recognize a gland type in the mammographic image to obtain a gland type recognition result. the breast benign and malignant detection model 102 is configured to: determine a prediction threshold corresponding to the breast benign and malignant detection model according to the gland type recognition result; and invoke the breast benign and malignant detection model after determining the prediction threshold to perform benign and malignant prediction on the CC-position mammographic image and the MLO-position mammographic image, to obtain the benign and malignant prediction result of the unilateral breast.

In embodiments, the gland type classification model is configured to: invoke the gland type classification model to recognize a gland type of the CC-position mammographic image to obtain a first gland type; invoke the gland type classification model to recognize a gland type of the MLO-position mammographic image to obtain a second gland type; and determine the first gland type or the second gland type which has a greater gland density as the gland type of the unilateral breast.

In some embodiments, the mammographic image assisted diagnosis apparatus further includes a lesion recognition model. The lesion recognition model is configured to perform lesion detection on the mammographic image to obtain a lesion detection result. The lesion detection includes at least one of lump detection and calcification detection.

In some embodiments, the lesion recognition model includes at least one of a lesion description model, a lesion benign and malignant model, a lesion matching model, and a lesion quadrant positioning model.

The lesion description model is configured to detect a lesion in the mammographic image to obtain lesion description information.

The lesion benign and malignant model is configured to perform benign and malignant recognition on the lesion in the mammographic image to obtain a lesion benign and malignant probability.

The lesion matching model is configured to determine the consistency of lesions of the CC-position mammographic image and the MLO-position mammographic image, to obtain a lesion matching probability.

The lesion quadrant positioning model is configured to perform quadrant calculation on the lesion in the mammographic image.

In some embodiments, the mammographic image assisted diagnosis apparatus further includes a nipple detection model. The nipple detection model is configured to recognize a nipple position in the mammographic image. The lesion quadrant positioning model is configured to perform quadrant calculation on the lesion in the mammographic image according to the nipple position.

In some embodiments, the mammographic image assisted diagnosis apparatus further includes a muscle detection model. The muscle detection model is configured to recognize, when the mammographic image is the MLO-position mammographic image, a muscle position in the mammographic image.

In some embodiments, the automatic report generation module 103 is configured to: receive a report correction request; and correct the detection report according to the report correction request.

In some embodiments, the automatic report generation module 103 is configured to: receive a local query request, the local query request being used for requesting to query a local area in the mammographic image; and output a detection report corresponding to the local area according to the local query request.

This application further provides a mammographic image processing apparatus. The mammographic image processing apparatus can be configured to implement the functions of the foregoing mammographic image processing method. The mammographic image processing apparatus includes:

an image obtaining module, configured to obtain a mammographic image of a unilateral breast, the mammographic image including: a CC-position mammographic image and an MLO-position mammographic image;

a target detection model, configured to process the CC-position mammographic image and the MLO-position mammographic image, to obtain an image detection result of the unilateral breast; and an automatic report output module, configured to generate a detection report according to the image detection result and output the detection report.

In some embodiments, the target detection model includes: a first single image detection component, a second single image detection component, a pooling layer, and a fully connected layer. A model detection model is configured to invoke the first single image detection component to process the CC-position mammographic image to obtain a first logits feature. A target detection model is configured to invoke the second single image detection component to process the MLO-position mammographic image to obtain a second logits feature. The breast benign and malignant detection model is configured to input the first logits feature and the second logits feature into the pooling layer and the fully connected layer to obtain the image detection result of the unilateral breast.

In some embodiments, the mammographic image processing apparatus further includes a gland type classification model. The gland type classification model is configured to recognize a gland type in the mammographic image to obtain a gland type recognition result. The target detection model is configured to: determine a prediction threshold corresponding to the target detection model according to the gland type recognition result; and invoke the target detection model after determining the prediction threshold to process the CC-position mammographic image and the MLO-position mammographic image, to obtain the image detection result of the unilateral breast.

In some embodiments, the gland type classification model is configured to: invoke the gland type classification model to recognize a gland type of the CC-position mammographic image to obtain a first gland type; invoke the gland type classification model to recognize a gland type of the MLO-position mammographic image to obtain a second gland type; and determine the first gland type or the second gland type which has a greater gland density as a gland type of the unilateral breast.

In some embodiments, the mammographic image processing apparatus further includes an abnormality recognition model. The abnormality recognition model is configured to perform abnormality detection on the mammographic image to obtain an abnormality detection result. The abnormality detection includes at least one of lump detection and calcification detection.

In some embodiments, the abnormality recognition model includes at least one of an abnormality description model, an abnormality classification model, an abnormality matching model, and an abnormality quadrant positioning model.

The abnormality description model is configured to detect an abnormality area in the mammographic image to obtain abnormality description information.

The abnormality classification model is configured to recognize an abnormality category in the mammographic image to obtain a corresponding category probability.

The abnormality matching model is configured to determine the consistency of abnormality areas of the CC-position mammographic image and the MLO-position mammographic image, to obtain an abnormality matching probability.

The abnormality quadrant positioning model is configured to perform quadrant calculation on the abnormality area in the mammographic image.

In some embodiments, the mammographic image processing apparatus further includes a nipple detection model. The nipple detection model configured to recognize a nipple position in the mammographic image. The abnormality quadrant positioning model is configured to perform quadrant calculation on the abnormality area in the mammographic image according to the nipple position.

In some embodiments, the mammographic image processing apparatus further includes a muscle detection model. The muscle detection model is configured to recognize, when the mammographic image is the MLO-position mammographic image, a muscle position in the mammographic image.

In some embodiments, the automatic report generation module 103 is configured to: receive a report correction request; and correct the detection report according to the report correction request.

In some embodiments, the automatic report generation module 103 is configured to: receive a local query request, the local query request being used for requesting to query a local area in the mammographic image; and output a detection report corresponding to the local area according to the local query request.

Figure 18:
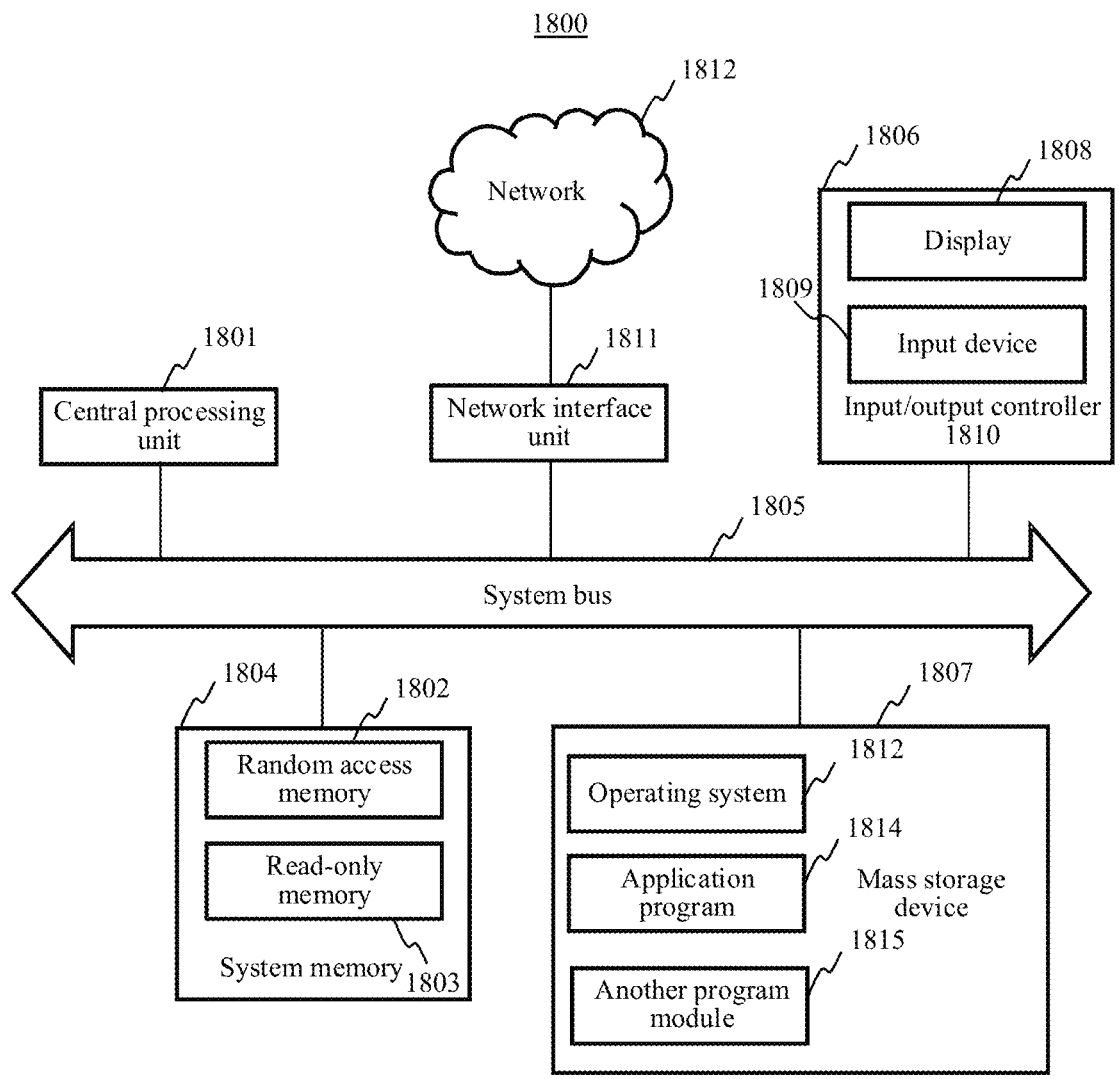
FIG. 18 is a block diagram of a computer device according to an exemplary embodiment of this application.

FIG. 18 is a schematic structural diagram of a computer device according to an exemplary embodiment of this application. In some embodiments, a computer device 1800 includes a central processing unit (CPU) 1801, a system memory 1804 including a random access memory (RAM) 1802 and a read-only memory (ROM) 1803, and a system bus 1805 connecting the system memory 1804 and the CPU 1801. The computer device 1800 further includes a basic input/output (I/O) system 1806 configured to transmit information between components in a computer, and a mass storage device 1807 configured to store an operating system 1813, a client 1814, and another program module 1815.

The basic I/O system 1806 includes a display 1808 configured to display information and an input device 1809 such as a mouse or a keyboard that is configured to input information by a user. The display 1808 and the input device 1809 are both connected to the CPU 1801 by using an input/output controller 1180 connected to the system bus 1805. The basic I/O system 1806 may further include the input/output controller 1180, to receive and process inputs from a plurality of other devices, such as the keyboard, the mouse, or an electronic stylus. Similarly, the I/O controller 1180 further provides an output to a display screen, a printer, or another type of output device.

The mass storage device 1807 is connected to the CPU 1801 by using a mass storage controller (not shown) connected to the system bus 1805. The mass storage device 1807 and an associated computer-readable medium provide non-volatile storage for the computer device 1800. That is, the mass storage device 1807 may include a computer-readable medium (not shown) such as a hard disk or a compact disc ROM (CD-ROM) drive.

Without loss of generality, the computer-readable medium may include a computer storage medium and a communication medium. The computer-storage medium includes volatile and non-volatile media, and removable and non-removable media implemented by using any method or technology used for storing information such as computer-readable instructions, data structures, program modules, or other data. The computer storage medium includes a RAM, a ROM, an erasable programmable ROM (EPROM), an electrically erasable programmable ROM (EEPROM), a flash memory or another solid-state memory technology, a CD-ROM, a digital versatile disc (DVD) or another optical memory, a tape cartridge, a magnetic cassette, a magnetic disk memory, or another magnetic storage device. Certainly, it may be known by a person skilled in the art that the computer storage medium is not limited to the foregoing several types. The system memory 1804 and the mass storage device 1807 may be collectively referred to as a memory.

According to the various embodiments of this application, the computer device 1800 may further be connected, through a network such as the Internet, to a remote computer on the network for running. That is, the computer device 1800 may be connected to a network 1812 by using a network interface unit 1811 connected to the system bus 1805, or may be connected to another type of network or a remote computer system (not shown) by using a network interface unit 1811.

In some embodiment, a computer device is provided, including a memory and a processor, the memory storing computer-readable instructions, the processor, when executing the computer-readable instructions, implementing the steps in the foregoing method embodiments.

In some embodiments, a computer-readable storage medium is provided, storing computer-readable instructions, the computer-readable instructions, when executed by a processor, implementing the steps in the foregoing method embodiments.

In some embodiments, a mammographic image assisted diagnosis system is further provided. The system includes: a breast DR device, a computer device, and a doctor device. The breast DR device is connected to the computer device, and the computer device is connected to the doctor device.

In some embodiments, a computer program product includes instructions that, when executed by one or more processors of a computer device, cause the computer device to perform the mammographic image assisted diagnosis method provided in the foregoing method embodiments.

A person of ordinary skill in the art may understand that all or some of the steps of the method embodiments may be implemented by hardware or a program instructing relevant hardware. The program may be stored in a computer-readable storage medium. The storage medium mentioned above may be a ROM, a magnetic disk, or an optical disc.

The foregoing descriptions are merely exemplary embodiments of this application, and are not intended to limit this application. Any modification, equivalent replacement, improvement and the like made within the spirit and principle of this application shall fall within the protection scope of this application.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

As used herein, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. The division of the foregoing functional modules is merely used as an example for description when the systems, devices, and apparatus provided in the foregoing embodiments performs imaging and/or prediction. In practical application, the foregoing functions may be allocated to and completed by different functional modules according to requirements, that is, an inner structure of a device is divided into different functional modules to implement all or a part of the functions described above.

What is claimed is:

1. A mammographic image assisted diagnosis method, performed by a computer device, the method comprising:
    obtaining a mammographic image of a unilateral breast, the mammographic image comprising: a cranial-caudal (CC)-position mammographic image and a mediolateral-oblique (MLO)-position mammographic image;
    invoking a gland type classification model to recognize a gland type in the mammographic image to obtain a gland type recognition result;
    determining a prediction threshold corresponding to a breast detection model according to the gland type recognition result; and
    invoking the breast detection model to perform a prediction of a condition of the unilateral breast according to the CC-position mammographic image and the MLO-position mammographic image and the prediction threshold;
    obtaining a prediction result of the unilateral breast, including a benign or malignant condition of the breast; and
    generating and outputting a detection report that includes the prediction result.

2. The method according to claim 1, wherein the breast detection model comprises a neural network that comprises: a first single image detection component, a second single image detection component, a pooling layer, and a fully connected layer; and
    invoking the breast detection model further comprises:
        invoking the first single image detection component to process the CC-position mammographic image to obtain a first feature;
        invoking the second single image detection component to process the MLO-position mammographic image to obtain a second feature; and
        inputting the first feature and the second feature into the pooling layer and the fully connected layer to obtain the benign and malignant prediction result of the unilateral breast.

3. The method according to claim 1, wherein invoking the gland type classification model further comprises:
    invoking the gland type classification model to recognize a gland type of the CC-position mammographic image to obtain a first gland type;
    invoking the gland type classification model to recognize a gland type of the MLO-position mammographic image to obtain a second gland type; and
    determining the first gland type or the second gland type which has a greater gland density as a gland type of the unilateral breast.

4. The method according to claim 1, further comprising:
    invoking a lesion recognition model to perform lesion detection on the mammographic image to obtain a lesion detection result, the lesion detection comprising at least one of: a lump detection and a calcification detection.

5. The method according to claim 4, wherein:
    the lesion recognition model comprises at least one of: a lesion description model, a lesion benign and malignant model, a lesion matching model, and a lesion quadrant positioning model; and
    invoking the lesion recognition model comprises one or more of:
        invoking the lesion description model to detect a lesion in the mammographic image to obtain lesion description information;
        invoking the lesion benign and malignant model to perform benign and malignant recognition on the lesion in the mammographic image to obtain a lesion benign and malignant probability;
        invoking the lesion matching model to determine the consistency of lesions of the CC-position mammographic image and the MLO-position mammographic image, to obtain a lesion matching probability; and
        invoking the lesion quadrant positioning model to perform quadrant calculation on the lesion in the mammographic image.

6. The method according to claim 5, wherein invoking the lesion recognition model comprises invoking the lesion quadrant positioning model, the method further comprising:
    prior to invoking the lesion quadrant positioning mode, invoking a nipple detection model to recognize a nipple position in the mammographic image; and
    invoking the lesion quadrant positioning model further comprises:
        invoking the lesion quadrant positioning model to perform quadrant calculation on the lesion in the mammographic image according to the nipple position.

7. The method according to claim 1, further comprises:
    when the mammographic image is the MLO-position mammographic image, invoking a muscle detection model to recognize a muscle position in the mammographic image.

8. The method according to claim 1, further comprising:
receiving a report correction request; and
correcting the detection report according to the report correction request.

9. The method according to claim 1, further comprising:
receiving a local query request, the local query request being used for requesting to query a local area in the mammographic image; and
outputting a detection report corresponding to the local area according to the local query request.

10. A computing device, comprising:
one or more processors; and
memory storing one or more programs that, when executed by the one or more processors, cause the one or more processors to perform operations comprising:
obtaining a mammographic image of a unilateral breast, the mammographic image comprising: a cranial-caudal (CC)-position mammographic image and a mediolateral-oblique (MLO)-position mammographic image;
invoking a gland type classification model to recognize a gland type in the mammographic image to obtain a gland type recognition result;
determining a prediction threshold corresponding to a breast detection model according to the gland type recognition result; and
invoking the breast detection model to perform a prediction of a condition of the unilateral breast according to the CC-position mammographic image and the MLO-position mammographic image and the prediction threshold;
obtaining a prediction result of the unilateral breast, including a benign or malignant condition of the breast; and
generating and outputting a detection report that includes the prediction result.

11. The computing device according to claim 10, wherein the breast detection model comprises a neural network that comprises: a first single image detection component, a second single image detection component, a pooling layer, and a fully connected layer; and
invoking the breast detection model further comprises:
invoking the first single image detection component to process the CC-position mammographic image to obtain a first feature;
invoking the second single image detection component to process the MLO-position mammographic image to obtain a second feature; and
inputting the first feature and the second feature into the pooling layer and the fully connected layer to obtain the benign and malignant prediction result of the unilateral breast.

12. The computing device according to claim 10, wherein invoking the gland type classification model further comprises:
invoking the gland type classification model to recognize a gland type of the CC-position mammographic image to obtain a first gland type;
invoking the gland type classification model to recognize a gland type of the MLO-position mammographic image to obtain a second gland type; and
determining the first gland type or the second gland type which has a greater gland density as a gland type of the unilateral breast.

13. The computing device according to claim 10, wherein the operations further comprise:

invoking a lesion recognition model to perform lesion detection on the mammographic image to obtain a lesion detection result, the lesion detection comprising at least one of: a lump detection and a calcification detection.

14. A non-transitory computer readable storage medium storing instructions that, when executed by one or more processors of a computing device, cause the one or more processors to perform operations comprising:
obtaining a mammographic image of a unilateral breast, the mammographic image comprising: a cranial-caudal (CC)-position mammographic image and a mediolateral-oblique (MLO)-position mammographic image;
invoking a gland type classification model to recognize a gland type in the mammographic image to obtain a gland type recognition result;
determining a prediction threshold corresponding to a breast detection model according to the gland type recognition result; and
invoking the breast detection model to perform a prediction of a condition of the unilateral breast according to the CC-position mammographic image and the MLO-position mammographic image and the prediction threshold;
obtaining a prediction result of the unilateral breast, including a benign or malignant condition of the breast; and
generating and outputting a detection report that includes the prediction result.

15. The computing device according to claim 10, wherein the operations further comprise:
when the mammographic image is the MLO-position mammographic image, invoking a muscle detection model to recognize a muscle position in the mammographic image.

16. The computing device according to claim 10, wherein the operations further comprise:
receiving a report correction request; and
correcting the detection report according to the report correction request.

17. The computing device according to claim 10, wherein the operations further comprise:
receiving a local query request, the local query request being used for requesting to query a local area in the mammographic image; and
outputting a detection report corresponding to the local area according to the local query request.

18. The non-transitory computer readable storage medium according to claim 14, wherein the breast detection model comprises a neural network that comprises: a first single image detection component, a second single image detection component, a pooling layer, and a fully connected layer; and
invoking the breast detection model further comprises:
invoking the first single image detection component to process the CC-position mammographic image to obtain a first feature;
invoking the second single image detection component to process the MLO-position mammographic image to obtain a second feature; and
inputting the first feature and the second feature into the pooling layer and the fully connected layer to obtain the benign and malignant prediction result of the unilateral breast.

19. The non-transitory computer readable storage medium according to claim 14, wherein invoking the gland type classification model further comprises:

invoking the gland type classification model to recognize a gland type of the CC-position mammographic image to obtain a first gland type;

invoking the gland type classification model to recognize a gland type of the MLO-position mammographic image to obtain a second gland type; and determining the first gland type or the second gland type which has a greater gland density as a gland type of the unilateral breast.

20. The non-transitory computer readable storage medium according to claim 14, further comprising:

invoking a lesion recognition model to perform lesion detection on the mammographic image to obtain a lesion detection result, the lesion detection comprising at least one of: a lump detection and a calcification detection.

\* \* \* \* \*